United States Patent [19]

Kondo et al.

[11] Patent Number: 4,496,658
[45] Date of Patent: Jan. 29, 1985

[54] METHOD FOR ENZYME IMMUNOASSAY AND PRODUCTION OF ANTIBODY

[75] Inventors: Koichi Kondo, Osaka; Susumu Iwasa, Tsuzuki; Isamu Yoshida, Hirakata, all of Japan

[73] Assignee: Takeda Chemical Industries, Ltd., Osaka, Japan

[21] Appl. No.: 311,327

[22] Filed: Oct. 14, 1981

[30] Foreign Application Priority Data

Oct. 15, 1980 [JP] Japan ............................ 55-144689
Jan. 14, 1981 [JP] Japan ............................ 56-4507

[51] Int. Cl.³ .................. G01N 33/54; G01N 33/56; G01N 33/58
[52] U.S. Cl. ............................ 436/510; 436/518; 436/531; 436/544; 436/545; 436/546; 436/547; 436/543; 436/800; 436/804; 436/808; 436/813; 436/814; 436/819; 435/7
[58] Field of Search .............. 424/1; 23/230 B; 436/510, 518, 536, 544–547, 800, 804, 808, 813, 814, 819; 435/4, 7

[56] References Cited

U.S. PATENT DOCUMENTS

| | | | |
|---|---|---|---|
| 3,935,074 | 1/1976 | Rubenstein et al. | 424/1 |
| 4,130,462 | 12/1978 | Rubenstein et al. | 424/1 |
| 4,161,515 | 7/1979 | Ullman | 424/1 |
| 4,200,436 | 4/1980 | Mochida et al. | 424/1 |
| 4,244,940 | 1/1981 | Jeong et al. | 436/534 |
| 4,310,455 | 1/1982 | Bahl | 424/1 |
| 4,315,908 | 2/1982 | Zer et al. | 424/1 |

OTHER PUBLICATIONS

Thanavala, et al., Chem. Abstracts, vol. 92, (Mar. 1980), #108860a.
Kitada, et al., Chem. Abstracts, vol. 95, (Jul. 1981), #25601w.
Matsuura et al., Endocrinology, vol. 104, (1979): 396–401.
Swaminathan et al., Biochemistry, vol. 17, (1978): 5832–38.
Ramakrishnan et al., Biochem. J., vol. 176, (1978): 599–602.

Primary Examiner—Christine M. Nucker
Attorney, Agent, or Firm—Wenderoth, Lind & Ponack

[57] ABSTRACT

In a method for immunochemical assay of human chorionic gonadotropin involving use of an antibody immobilized on a carrier, an antigen and an antibody to which a labeling agent has been attached, when the antibody supported on the carrier and the antibody coupled to a labeling agent are different antibodies which are not overlapping in antigen-determining site and one of said different antibodies is specifically reactive to human chorionic gonadotropin, a high reproducibility of the result of the immunochemical assay is obtained.

8 Claims, 7 Drawing Figures

METHOD FOR ENZYME IMMUNOASSAY AND PRODUCTION OF ANTIBODY

BACKGROUND OF THE INVENTION

This invention relates to a method for immunochemical assay of human chorionic gonadotropin (hereinafter briefly, hCG) and to production of an antibody usable for the assay.

hCG is a proteohormone produced from chorionic cells formed on conception, and stimulates secretion of progesterone. Detection of hCG is a technique commonly utilized as an early diagnostic procedure for pregnancy. Furthermore, in chorionic diseases such as hydatidiform mole, destructive mole, villous cancer, etc. determination of hCG in the urine, blood or other body fluid has proved to be very beneficial for an early detection of such disorders, evaluation of effects of treatments and prognostic management of the diseases. However, for diagnosis of these diseases, a detection sensitivity of less than about 100 IU/l of hCG is required and there is the problem of immunological cross-reactivity with other proteohormones structurally analogous to hCG, such as luteinizing hormone (hereinafter sometimes referred to as hLH), follicle stimulating hormone (hereinafter sometimes referred to as hFSH) and thyroid stimulating hormone (hereinafter sometimes referred to as hTSH). Among them, hLH, in particular, is very similar to hCG and the amount of hLH in physiological urine may at times be as high as 150 IU/l. Therefore, in order to measure hCG in the body fluid, it is necessary to distinguish hCG from hLH in an immunological sense.

On the other hand, chemical analyses of these proteohormones have shown that the above-mentioned cross-reactivity is due to their α-subunits which structurally have much in common. Therefore, the comparatively less analogous β-subunit of hCG (hereinafter sometimes referred to as hCG-β) was separated and purified and an anti-hCG-β antibody was prepared and used for specific detection of hCG. However, the separation and purification of hCG-β requires a complicated procedure and it is also very difficult to avoid contamination with hCG and the α-subunit of hCG (hereinafter sometimes referred to as hCG-α). The concomitant presence of these impurities and the still remaining common amino acid sequence of the β-subunits of hCG and hLH do not allow the cross-reactivity with hLH to be eliminated completely with use of the anti-hCG-β antibody. However, the peptide fragment consisting of about 30 amino acid residues at the C-terminal of hCG-β has an amino acid sequence not found in hLH, and it was found that, in this particular moiety, hCG can be completely differentiated from hLH.

Based on these results of structural analysis, Matsuura et al. synthesized the C-terminal peptide of hCG-β, immunized rabbits with the peptide and carried out radioimmunoassays (hereafter briefly, RIA) with the resulting hCG-specific antiserum by the competitive method [Endocrinology, Vol. 104 (1979), P. 396]. Though they obtained satisfactory results as to specificity, the sensitivity obtained was not sufficient.

In European patent application No. 81,102,360.5, the anti-hCG antibody obtained by immunization of an animal with hCG is contacted with the solid phase obtained by immobilizing the synthetic C-terminal peptide of hCG-β, and the anti-hCG antibody specifically absorbed is used in competitive enzyme immunoassays (hereafter sometimes briefly referred to EIA) with satisfactory specificity and sensitivity. However, RIA and EIA by the competitive method are liable to be influenced by other components in test fluids and, as an additional disadvantage, require prolonged times for assays. Therefore, the present inventors sought a more expedient method of assay. The investigation led to the finding that hCG could be assayed with high specificity and sensitivity by the non-competitive method (hereafter referred to as the sandwich method). This invention has been accomplished on the basis of the above finding.

SUMMARY OF THE INVENTION

This invention relates to:

1. In a method for immunochemical assay of human chorionic gonadotropin involving use of an antibody immobilized on a carrier, an antigen and an antibody to which a labeling agent has been attached, an improvement which comprises using as the antibody supported on the carrier and the antibody coupled to the labeling agent different antibodies which are not overlapping in antigen-determining site, and wherein one of said different antibodies is specifically reactive to human chorionic gonadotropin;

2. A method of producing an antibody specifically reactive to human chorionic gonadotropin, which comprises condensing a peptide of general formula [I]:

H-R-Pro-Ser-Asp-Thr-Pro-Ile-Leu-Pro-Gln-OH

[wherein R is a partial peptide of 1 to 14 amino acid residues including Gly in the 14-position of the peptide $Ala^1$-$Pro^2$-$Pro^3$-$Pro^4$-$Ser^5$-$Leu^6$-$Pro^7$-$Ser^8$-$Pro^9$-$Ser^{10}$-$Arg^{11}$-$Leu^{12}$-$Pro^{13}$-$Gly^{14}$] with a carrier protein in the presence of glutaraldehyde, immunizing a warm-blooded animal other than man with the condensation product to produce an antibody and isolating the same antibody; and 3. An assay kit for the immunochemical assay of hCG by the sandwich method, which comprises
   (1) An antibody immobilized on a carrier,
   (2) An antibody labeled with a labeling agent, wherein the antibody used in reagent (1) and the antibody used in reagent (2) are different antibodies which are not overlapping in antigen-determining site, and one of said different antibodies is specifically reactive to human chorionic gonadotropin,
   (3) A standard hCG of 0 to 100 IU,
   (4) A buffer for dilution of reagents (1) to (3) and the test fluid,
   (5) A buffer for use in the washing of the carrier after incubation, and
   (6) When the labeling agent is an enzyme, reagents used in measuring the activity of the enzyme; When a fluorescent substance is used as the labeling agent, materials for measuring the intensity of fluorescence; When a luminous substance is used as the labeling agent, an oxidizing agent, a catalyst and a buffer for dissolving the oxidizing agent as well as the catalyst.

3

Figure 4:
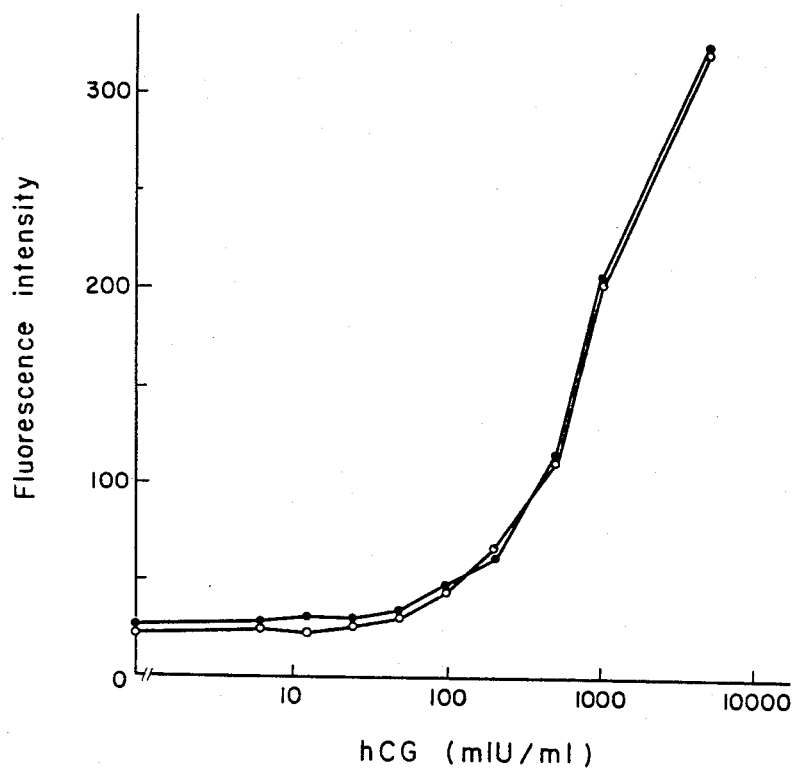
Figure 5:
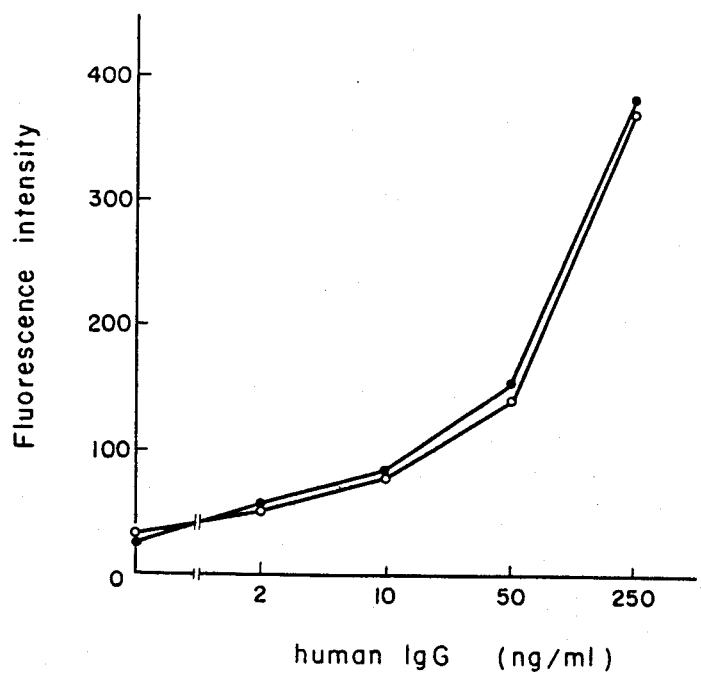
Figure 6:
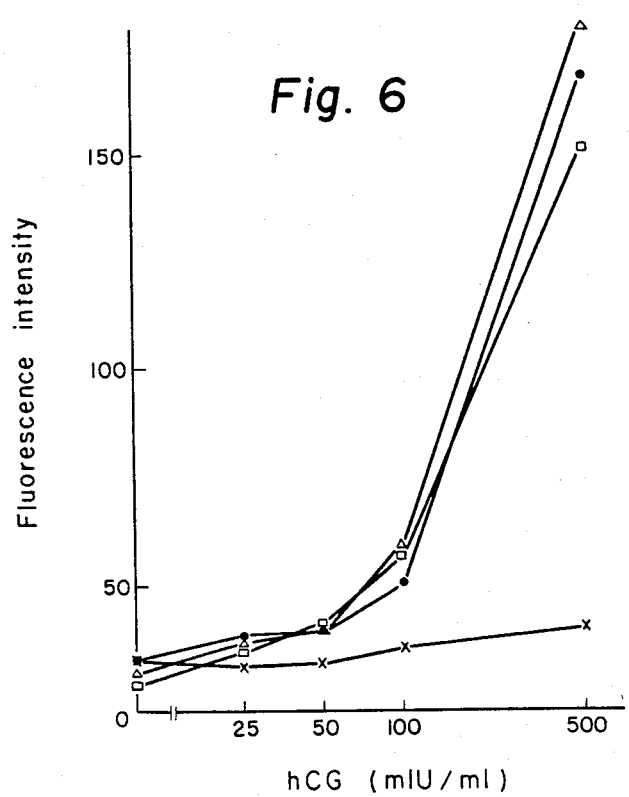

FIGS. 4-6 show curves obtained from EIA methods with respect to hCG and human IgG.

Figure 7:
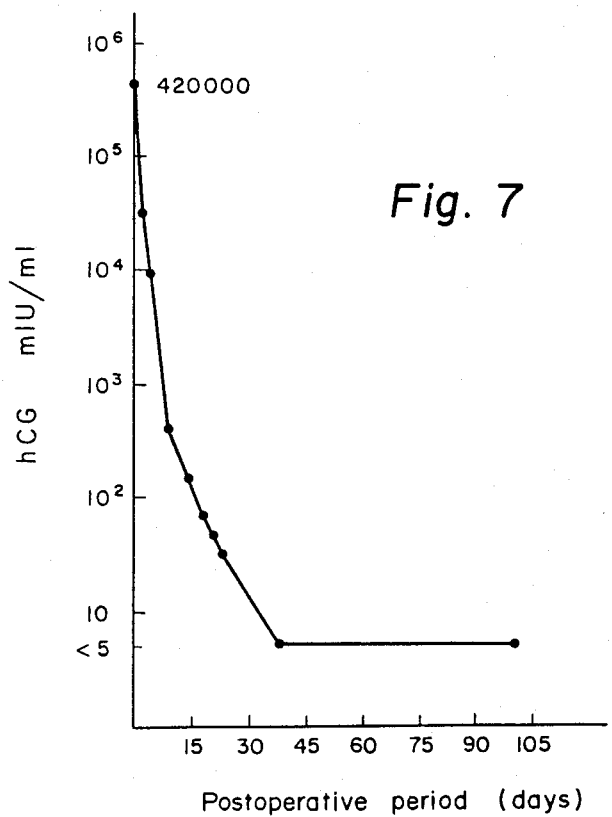

FIG. 7 shows postoperative hCG levels in a patient.

DETAILED DESCRIPTION OF THE INVENTION

The principles of the competitive method and sandwich method of assay, to which reference is often made in this specification, will be described below.

(1) Competitive method:

A test fluid containing an unknown amount of an antigen and a known amount of the antigen labeled with a labeling agent are allowed to undergo competitive reaction with a known amount of the corresponding antibody and the activity of the labeling agent attached to the antibody or the activity of the free labeling agent is determined.

(2) Sandwich method:

A test fluid containing an unknown amount of an antigen is reacted with an excess of the antibody immobilized on a carrier (first reaction) and, then, with a known excess amount of the antibody labeled with a labeling agent (second reaction). The activity of the labeling agent combined on the carrier or that of the labeling agent not combined is determined. The first and second reactions may be conducted simultaneously or one after another.

Generally in the immunochemical assay by the sandwich method, the antibody used in the first reaction and the antibody for the second reaction are the same antibody prepared from the same antiserum. However, in the present sandwich method for specific immunochemical assay, for the purpose of eliminating the assay error due to cross-reactivity with structurally similar proteohormones such as hLH, the first and second reactions are conducted using different antibodies which are not overlapping in antigen-determining site, and one of the different antibodies is specifically reactive to hCG.

An example (1) of the antibody specifically reactive to hCG is the antibody described in Endocrinology, Vol. 104 (1979), P. 396. Thus, an hCG-specific peptide at the C-terminal of hCG-$\beta$ subunit and a carrier protein such as bovine albumin or bovine-thyroglobulin are condensed in the presence of a water-soluble carbodiimide reagent such as 1-ethyl-3-(3-dimethylaminopropyl)-carbodiimide, and using the resulting condensate and Freund's complete adjuvant or incomplete adjuvant, a warm-blooded animal such as a rabbit is immunized a plurality of times to produce an antibody. This procedure gives an antiserum which reacts specifically to hCG.

(2) The hCG-specific anti-hCG antibody described in European patent application 81,102,360.5 is mentioned. This antibody is prepared as follows. The peptide of general formula [I]:

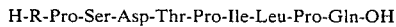
H-R-Pro-Ser-Asp-Thr-Pro-Ile-Leu-Pro-Gln-OH

[wherein R is a partial peptide of 1 to 14 amino acid residues including 14-Gly of the peptide $Ala^1$-$Pro^2$-$Pro^3$-$Pro^4$-$Ser^5$-$Leu^6$-$Pro^7$-$Ser^8$-$Pro^9$-$Ser^{10}$-$Arg^{11}$-$Leu^{12}$-$Pro^{13}$-$Gly^{14}$], as immobilized on a carrier, is contacted with a body fluid containing an anti-hCG antibody and the anti-hCG antibody specifically absorbed is separated by elution.

As examples of the peptide fragments of 1 to 14 amino acid residues including Gly in the 14-position of peptide R [i.e. $Ala^1$-$Pro^2$-$Pro^3$-$Pro^4$-$Ser^5$-$Leu^6$-$Pro^7$-$Ser^8$-$Pro^9$-$Ser^{10}$-$Arg^{11}$-$Leu^{12}$-$Pro^{13}$-$Gly^{14}$] which is employed in the production of a specific antibody to hCG, there may be mentioned Gly, Pro-Gly, Leu-Pro-Gly, Arg-Leu-Pro-Gly, Ser-Arg-Leu-Pro-Gly, Pro-Ser-Arg-Leu-Pro-Gly, Ser-Pro-Ser-Arg-Leu-Pro-Gly, Pro-Ser-Pro-Ser-Arg-Leu-Pro-Gly, Leu-Pro-Ser-Pro-Ser-Arg-Leu-Pro-Gly, Ser-Leu-Pro-Ser-Pro-Ser-Arg-Leu-Pro-Gly, Pro-Ser-Leu-Pro-Ser-Pro-Ser-Arg-Leu-Pro-Gly, Pro-Pro-Ser-Leu-Pro-Ser-Pro-Ser-Arg-Leu-Pro-Gly, Pro-Pro-Pro-Ser-Leu-Pro-Ser-Pro-Ser-Arg-Leu-Pro-Gly, Ala-Pro-Pro-Pro-Ser-Leu-Pro-Ser-Pro-Ser-Arg-Leu-Pro-Gly.

Throughout this specification, when abbreviations are used for amino acids, peptides, protective groups, active groups, etc., they are either the abbreviations according to IUPAC-IUB Commission on Biological Nomenclature or the abbreviations of common use in this field of art. The following is a partial list of the abbreviations. It is to be understood that when optical isomers exist in regard to amino acids, etc., L-forms are meant unless otherwise indicated.

Ala: alanine
Pro: proline
Ser: serine
Leu: leucine
Arg: arginine
Gly: glycine
Asp: aspartic acid
Thr: threonine
Ile: isoleucine
Gln: glutamine
Glu: glutamic acid
Tyr: tyrosine
Met: methionine
Nle: norleucine
Phe: phenylalanine
Val: valine
Trp: tryptophan
Asn: Asparagine
Lys: lysine
His: histidine
Z: benzyloxycarbonyl
$OBu^t$: t-butyl ester
HONB: N-hydroxy-5-norbornene-2,3-dicarboxyimide
ONB: N-hydroxy-5-norbornene-2,3-dicarboximide ester
DMF: N,N'-dimethylformamide
DCC: N,N'-dicyclohexylcarbodiimide
DMSO: dimethylsulfoxide
THF: tetrahydrofuran
HOBt: 1-hydroxy-benzotriazole
OSu: N-hydroxysuccinimide ester
ECDI: 1-ethyl-3-(3-dimethylaminopropyl)carbodiimide
CMCT: 1-cyclohexyl-3-(2-morpholinoethyl)carbodiimide metho-para-toluenesulfonate
GLA: glutaraldehyde
m-MBHS: meta-maleimidobenzoyl-N-hydroxysuccinimide ester
p-MCHS: para-maleimidomethylcyclohexane-1-carboxyl-N-hydroxysuccinimide ester The various peptides which are employed for the production of the specific antibody according to the present invention can be produced by procedures known per se. While both of the solid-phase and the liquid-phase methods of synthesis may be employed, the latter method is more often advantageous. Such methods for peptide synthesis include those described in the literature, e.g. Schröder and Lubke: The Peptides, Vol. 1 (1966), Academic Press, New York, U.S.A. and Izumiya et al: "Peptide Gosei" (Peptide Synthesis) (1975), Maruzen Inc., Japan, namely the azide method, chloride method, acid anhydride method, mixed acid anhydride method, DCC method, active ester method, Woodward Reagent K method, carbodiimidazole method, reduction-oxidation method, DCC-additive (e.g. HONB, HOBt, HOSu) method and so on.

The carrier used for the production of the specific antibody according to the present invention includes, among others, beads of gels {for example, agarose gel [e.g. Sepharose 4B, Sepharose 6B (Pharmacia Fine Chemicals, Sweden)], dextran gel [e.g. Sephadex G75, Sephadex G100, Sephadex G200 (Pharmacia Fine Chemicals)], polyacrylamide gel [e.g. Biogel P30, Biogel P60, Biogel P100 (Bio-Rad Laboratories, U.S.A.]}, particles of cellulose [for example, Avicel (Asahi Kasei Inc. Japan), ion exchange cellulose (e.g. diethylaminoethyl-cellulose, carboxymethyl-cellulose)], physical adsorbents [for example, glass beads, glass rods, aminoalkyl-glass beads, aminoalkyl-glass rods), silicone rubbers, styrene resin (e.g. polystyrene beads, polystyrene granules)], ion exchange resins {for example, weakly acid cation exchange resins [e.g. Amberlite IRC-50 (Rohm and Hass, U.S.A.), Zeocarb 226 (Permutit, West Germany)], weakly basic anion exchange resins [e.g. Amberlite IR-4B (Rohm and Hass), Dowex 3 (Dow Chemical, U.S.A.)]} and so on.

Immobilization of the peptide on such a carrier can be accomplished in the conventional manner. Among the known methods for the preparation of immobilized peptides are those described e.g. in "Metabolism" 8 (1971) page 696. For example, the cyanogen bromide method, GLA method, DCC method, etc. may be employed. The preferred method comprises activating the carrier with cyanogen bromide and causing the peptide to be coupled to the activated carrier.

Then, a body fluid (e.g. serum, plasma, ascites) containing anti-hCG antibody obtained by immunizing hCG to an animal (e.g. cattle, horse, sheep, rabbit, rat, guinia pig, dog, pig, monkey) is contacted with the peptide of the formula [I] which has already been immobilized on a carrier. The body fluid is precipitated by salting-out with sodium sulfate or ammonium sulfate, and the precipitate thus obtained is subjected to column chromatography using, for example, DEAE-cellulose to recover IgG-containing fractions, and the fractions are contacted with the above immobilized peptide to absorb a specific anti-hCG antibody. This procedure removes anti-hCG antibodies which are cross-reactive to hLH, hFSH and hTSH.

The specific anti-hCG antibody absorbed on the solid phase is recovered by elution. The elution is carried out by using, for instance, a buffer solution of low pH or high pH (e.g. 0.17M glycine-hydrochloric acid buffer of pH 2.3, an aqueous ammonia at pH 11), or a buffer solution containing a high concentration of a salt. The elution gives fractions of the specific antibody. The above procedure may be carried out batchwise or by means of a column.

The physical properties of the antibody obtained above are as follows. (1) In Ouchterlony test ["Ikagaku Jikkenho Koza", (Method in Medical Chemistry) Vol. 4 p. 159 (1972), published by Nakayama Shoten, Japan], it gives precipitation lines with hCG and hCG-β; (2) in electrophoresis, it belongs to the gamma-globulin fraction; (3) it can be mixed with hCG-sensitized erythrocytes to agglutinate the erythrocytes; (4) it has a molecular weight of about 140,000 to 170,000 and contains about 2 to 7 percent of sugar; (5) it is readily soluble in aqueous medium at pH 2 to 12; (6) it is stable under refrigeration for at least one year; (7) it has the ultraviolet absorption spectrum given in FIG. 1; (8) its amino acid analysis shows that per 100 moles of glycine, it contains 85 to 97 moles of lysine, 35 to 43 moles of histidine, 38 to 45 moles of arginine, 110 to 132 moles of aspartic acid, 98 to 107 moles of threonine, 118 to 135 moles of serine, 138 to 145 moles of glutamic acid, 92 to 134 moles of proline, 100 moles of glycine, 73 to 79 moles of alanine, 129 to 138 moles of valine, 2 to 10 moles of methionine, 28 to 37 moles of isoleucine, 100 to 112 moles of leucine, 38 to 48 moles of tyrosine, and 55 to 68 moles of phenylalanine; and (9) its molecule consists of two H- and two L-chains as linked by S—S bonds.

As an antibody which reacts specifically with hCG, there may be mentioned the antibody prepared by condensing a peptide of general formula [I]:

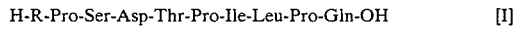

H-R-Pro-Ser-Asp-Thr-Pro-Ile-Leu-Pro-Gln-OH      [I]

[wherein R is a partial peptide of 1 to 14 amino acid residues including 14-Gly of the peptide $Ala^1$-$Pro^2$-$Pro^3$-$Pro^4$-$Ser^5$-$Leu^6$-$Pro^7$-$Ser^8$-$Pro^9$-$Ser^{10}$-$Arg^{11}$-$Leu^{12}$-$Pro^{13}$-$Gly^{14}$] with a carrier protein in the presence of glutaraldehyde (hereafter briefly, GLA), inoculating a warm-blooded animal other than man with the resulting condensate to produce an antibody and recovering the same. The carrier protein referred to above is a substance which is used as coupled to a hapten (a substance of low molecular weight) for producing an antibody to the hapten such as a peptide which, as it is alone, cannot induce formation of an antibody, and includes such proteins as bovine serum albumin, bovine gamma-globulin, bovine thyroglobulin, tetanus toxoid, hemocyanine and polyamino acid.

The coupling of the peptide of general formula [I] with a carrier protein in the presence of GLA can be conducted by the conventional method [e.g. "Hormone and Metabolic Research", Vol. 8 (1976), P.241]. The relative amount of peptide [I] and carrier protein is preferably 1:1 to 2:1, and the reaction pH of about 7.3 gives satisfactory results in many cases. The reaction time is somewhere between 2 and 6 hours and a reaction time of 3 hours is usually appropriate. The condensation product thus obtained is dialyzed against water of about 4° C., lyophilized and stored as usual.

The condensation product thus obtained is used to inoculate a warm-blooded animal other than man.

The warm-blooded animal other than man which is used in the production of the above hCG-specific antibody includes, among others, mammarian warm-blooded animals (e.g. rabbit, sheep, rat, mouse, guinea pig, cattle, horse, pig) and avian species (e.g. chicken, pigeon, duck, goose, quail).

To inoculate the condensation product into such a warm-blooded animal other than man, the condensation product is used in an amount sufficient to produce the desired antibody. For example, 2 mg per dose of the condensation product is emulsified with equal volumes (1 ml) of physiological saline and Freund's complete adjuvant and the emulsion is injected subcutaneously into dorsal sites and rear foot pads of a rabbit for a total of 5 times at intervals of 4 weeks. The above procedure yields the desired antibody in many instances.

The antibody thus produced in the body of the warm-blooded animal can be harvested as follows. Thus, in the case of a rabbit, for instance, blood is withdrawn from the ear vein and centrifuged to separate the serum normally at a time between 7 to 12 days after the last immunization.

The carrier for supporting the antibody used as immobilized thereon in the assay of hCG may be any of the carriers mentioned for the production of the antibody.

The coupling of the carrier with the antibody may be effected by the conventional method. For example, the cyanogen bromide method as well as the GLA method described in Metabolism, Vol. 8 (1971), P.696 may be mentioned. As a more expedient procedure, the antibody may be physically adsorbed on the surface of the carrier.

The antigen-containing test fluid to be assayed by the sandwich method includes urine, serum, plasma, spinal fluid, etc. and is, usually, serum.

The labeling agent for said labeled antibody which is used in the assay of hCG includes, for instance, radioisotopes, enzymes, fluorescent substances and luminous substances. Examples of such radioisotopes are $^{125}I$, $^{131}I$, $^{3}H$ and $^{14}C$.

The labeling agent is desirably an enzyme which is stable and has a high specific activity. Thus, there may be mentioned, for example, (1) carbohydrase [for example, glycosidase (e.g. $\beta$-galactosidase, $\beta$-glucosidase, $\beta$-glucuronidase, $\beta$-fructosidase, $\alpha$-galactosidase, $\alpha$-glucosidase, $\alpha$-mannosidase), amylase (e.g. $\alpha$-amylase, $\beta$-amylase, isoamylase, glucoamylase, Taka-amylase A), cellulase, lysozyme], (2) amidase (e.g. urease, asparaginase), (3) esterase [for example, cholinesterase (e.g. acetylcholinesterase), phosphatase (e.g. alkaline phosphatase), sulfatase, lipase], (4) nuclease (e.g. deoxyribonuclease, ribonuclease), (5) iron-prophyrin enzymes (e.g. catalase, peroxidase, cytochrome oxidase), (6) copper enzymes (e.g. tyrosinase, ascorbic acid oxidase), (7) dehydrogenase (e.g. alcohol dehydrogenase, malic acid dehydrogenase, lactic acid dehydrogenase, isocitric acid dehydrogenase), etc. The fluorescent substance may for example be fluorescamine, fluorescence isothiocyanate, etc. and the luminous substances include, among others, luminol, luminol derivatives, luciferin, lucigenin, etc.

The coupling of the hCG-specific antibody with the labeling agent can be effected by the conventional method, e.g. the chloramine T method [Nature, 194 (1962), p.495], periodic acid method [Journal of Histochemistry and Cytochemistry 22 (1974), p. 1084], maleimide method [Journal of Biochemistry 79 (1976), p.233].

To conduct the specific immunochemical assay of hCG and hCG-$\beta$ by the sandwich method, the test fluid is first reacted with a solid phase to which the antibody has been coupled either chemically or physically by the conventional procedure (first reaction). Then, after the solid phase is washed, a known quantity of the labeled antibody is added and reacted (second reaction). Then, usually, the solid phase is washed well and the activity of the labeling agent is determined. If the labeling agent is a radioisotope, its activity is measured with a well counter or a liquid scintillation counter. If the labeling agent is an enzyme, a substrate is added, the mixture is allowed to stand and the enzymatic activity is assayed colorimetrically or fluorometrically. In case the labeling agent is a fluorescent substance or a luminous substance, these are measured by the conventional methods. In the above assay procedure, the washing of the solid phase as an intermediate process between the first and the second reaction may be omitted or, for further simplification, the test fluid, antibody-bound solid phase and the labeled antibody may be simultaneously reacted. Thus, since the antibodies used according to this invention are dissimilar in antigen-determining site, assay results are not influenced by the order and time of additions, the interposition or omission of the washing process, etc.

When $\beta$-galactosidase (hereinafter sometimes abbreviated to $\beta$-Gal) is used as the labeling agent in the antibody to which the labeling agent has been attached, a lyophilyzed one is preferable because the lyophilizate is stable.

The lyophilizate according to this invention is produced by lyophilizing an aqueous composition which comprises the antibody to which $\beta$-Gal has been attached and sugar or sugar alcohol.

As examples of the sugar employed in the practice of this invention, there may be mentioned pentoses such as arabinose, xylose, ribose, etc., hexoses such as glucose, fructose, mannose, galactose, rhamnose, etc.; disaccharides such as maltose, cellobiose, trehalose, gentiobiose, lactose, sucrose, etc.; and trisaccharides such as raffinose, maltotriose, etc. The sugar alcohol includes monosaccharides of 5 carbon atoms, e.g. xylitol, monosaccharides of 6 carbon atoms, e.g. sorbitol, mannitol, inositol, etc. Particularly preferred are arabinose, mannitol, inositol, sucrose and raffinose, and more especially desirable is sucrose. The above-mentioned sugar and sugar alcohol may be used as a mixture.

The $\beta$-Gal containing aqueous composition according to this invention may further contain albumin in addition to said sugar or/and sugar alcohol, and may still further contain magnesium or/and calcium ion donors or precursors. Allowing these additional component or components to be present in the composition helps prevent decrease of enzymatic activity in the course of lyophilization and, in the case of a conjugate of $\beta$-Gal and immunoactive material, prevent decrease of immunological activity, in addition to the effect of contributing to an improved shape of the lyophilizate. As examples of the abovementioned albumin, there may be mentioned such serum albumins as human serum albumin, horse serum albumin, bovine serum albumin, sheep serum albumin, etc., although bovine serum albumin is preferred. The above-mentioned magnesium or/and calcium ion donors or precursors include any and all compounds capable of liberating magnesium or/and calcium ions, although magnesium salts and calcium salts may be normally employed. Preferred are magnesium chloride and calcium chloride.

In the aqueous composition of this invention, the content of $\beta$-Gal is an amount equivalent to 10 pg to 1 mg (or 0.3 microunit to 30 milliunits) per ml of the composition, and preferably 100 pg to 10 $\mu$g (or 3 microunits to 0.3 milliunit) on the same basis. The content of sugar or sugar alcohol is usually equivalent to a concentration of 0.01 to 20 w/v % in the aqueous composition and preferably 0.2 to 5 w/v % on the same basis. The content of albumin is usually equivalent to a concentration of 0.01 to 5 w/v % and preferably 0.1 to 1 w/v % in the aqueous composition. The concentration of said magnesium or/and calcium ion donors in the aqueous composition is 0.0001 to 0.1M/l and preferably 0.0001 to 0.01M/l.

In preparing the aqueous composition, the order of addition of the components is not critical.

The lyophilizate according to this invention is produced by lyophilizing the above aqueous composition at about −30° C. to −50° C. and, then, removing the ice by sublimation under reduced pressure at a temperature of about 10° C. to 20° C. in the conventional manner. After this freeze-drying process, nitrogen gas sealing or vacuum sealing is preferably performed to prevent spoilage and degradation due to microorganisms such as fungi and bacteria. The nitrogen gas sealing is usually accomplished by purging the lyophilizate sufficiently with nitrogen gas and sealing it in a nitrogen gas atmosphere. The vacuum sealing is usually done by sealing the lyophilizate under reduced pressure (e.g. 10 to 0.01 mmHg).

The resultant lyophilizate obtained by freeze-drying the aqueous composition is very useful as an assay reagent because the enzymatic activity of β-Gal has been substantially kept intact.

The lyophilizate obtained by freeze-drying the aqueous composition containing a β-Gal-immunoactive material conjugate and a sugar or a sugar alcohol is useful as a diagnostic reagent, and because of its comparatively low price and high specific activity, is of value as a reagent for EIA.

Thus the assay method of this invention is very advantageous.

Thus, in accordance with this invention, the following advantages can be realized.

(1) Trace amounts of hCG and hCG-β can be assayed without interferences from hLH and other peptide hormones structurally related to hCG.

(2) Because the sandwich method, in contrast to the competitive method, is employed, the assay can be carried out over a broad concentration range.

(3) The assay method is easy and it takes a short time for the assay, because two kinds of antibodies and an antigen can be simultaneously reacted.

(4) Accordingly, the assay method is applicable to a broad range of applications such as an early diagnosis and prognostic management of chorionic diseases including villous cancer.

The assay kit for the immunochemical assay of hCG by the sandwich method in accordance with this invention comprises (1) The antibody immobilized on a carrier,
(2) The antibody labeled with a labeling agent,
(3) The standard hCG of 0 to 100 IU,
(4) The buffer for dilution of reagents (1) to (3) and the test fluid. [This may be any buffer solution which can be used for diluting these reagents and test fluid; phosphate buffer and glycine buffer at pH 6 to 9 may be mentioned as examples.]
(5) The buffer for use in the washing of the carrier after incubation. [This may be any buffer solution that can be used for washing the carrier; phosphate or glycine buffer may be mentioned as an example.]
(6) When the labeling agent is an enzyme, the reagents used in measuring the activity of the enzyme. For example, when the enzyme is β-D-galactosidase, the substrate (preferably 4-methylumbelliferyl β-D-galactoside or o-nitrophenyl β-D-galactoside), the buffer for dissolving the substrate (preferably, phosphate buffer) and the buffer for terminating the enzymatic reaction (preferably, carbonate buffer or glycine buffer). When a fluorescent substance is used as the labeling agent, the materials for measuring the intensity of fluorescence. When a luminous substance is used at the labeling agent, for example, in the case of luminol, the oxidizing agent (preferably, hydrogen peroxide), the catalyst (preferably, micro-peroxidase or a hypochlorite) and the buffer for dissolving the oxidizing agent as well as catalyst (preferably, sodium hydroxide TS or carbonate buffer) are used.

It should be understood that (1) and (2) may be a premix.

The above kit is preferably used in the following manner.

10 to 200 μl of the standard hCG or test fluid is diluted with reagent (4), followed by addition of a known amount of reagent (1) and about 10 to 300 μl of reagent (2). The reaction is conducted at 0° to 40° C. for about 1 to 24 hours. Then, the carrier is washed with reagent (5) and the activity of the labeling agent combined to the carrier is measured. When the labeling agent is a radioisotope, a well counter or a liquid scintillation counter is employed. When the labeling agent is an enzyme, about 10 to 1000 μl of the substrate solution is added, the reaction is conducted at 20° to 40° C. for about 0.5 to 24 hours, the enzymatic reaction is then terminated, and the absorbance or fluorescence intensity of the reaction mixture is determined. When the labeling agent is a fluorescent or luminous material, it can be measured by the method known per se.

The following examples and reference examples are merely intended to describe the present invention in further detail and should by no means be construed as limiting the scope of the invention.

In the reference examples presented below, thin-layer chromatography was carried out using the silica gel plate 60F$_{254}$ from Merck and the following eluents.

Rf$^1$: chloroform-methanol=95:5
Rf$^2$: chloroform-methanol-acetic acid=9:1:0.5
Rf$^3$: ethyl acetate-pyridine-acetic acid-water=60:20:6:10
Rf$^4$: n-butanol-pyridine-acetic acid-water=30:20:6:24
Rf$^5$: ethyl acetate-n-butanol-acetic acid-water=1:1:1:1
Rf$^6$: n-butanol-acetic acid-water=12:3:5

REFERENCE EXAMPLE 1

Production of H-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln-OH [hereinafter referred to as peptide (I), the C-terminal fragment peptide of hCG-β (123-145)]:

(a) Production of Z-Pro-Gln-OBu$^t$:

In 500 ml of methanol is dissolved 12.5 g of Z-Gln-OBu$^t$ and catalytic reduction is carried out with palladium black as catalyst. The catalyst is filtered off, the solvent distilled off and the residue dissolved in 300 ml of ethyl acetate. To this solution is added 200 ml of an ethyl acetate solution of Z-Pro-ONB (prepared from 9.7 g of Z-Pro-OH, 8.4 g of HONB and 8.8 g of DCC) and the mixture is stirred for 5 hours. The reaction mixture is washed with 0.2N-HCl, 4% aqueous sodium hydrogen carbonate and water in that order, followed by drying over anhydrous sodium sulfate. The ethyl acetate is then distilled off, and the residue is crystallized by the addition of petroleum benzine and a small amount of diethyl ether and further recrystallized from the same solvent system.

Yield 13.1 g (81.5%), m.p. 86°–88° C., $[\alpha]_D^{26} -64.8°$ (c=0.5, methanol), $Rf^1$ 0.42, $Rf^2$ 0.73.

Elemental analysis (for $C_{22}H_{31}O_6N_3$): Calcd. C, 60.95; H, 7.21; N, 9.69; Found C, 61.04; H, 7.20; N, 9.49.

(b) Production of Z-Leu-Pro-Gln-OBu$^t$:

In 500 ml of methanol is dissolved 13 g of Z-Pro-Gln-OBu$^t$ and catalytic reduction is carried out in hydrogen gas streams using palladium black as catalyst. The catalyst is filtered off, the solvent distilled off and the residue dissolved in 300 ml of ethyl acetate. To this solution is added an ethyl acetate solution of Z-Leu-ONB (prepared from 7.9 g of Z-Leu-OH, 6.5 g of HONB and 6.8 g of DCC) and the mixture is stirred for 5 hours. The reaction mixture is washed with 0.2N-HCl, 4% aqueous sodium hydrogen carbonate and water in that order, followed by drying over anhydrous sodium sulfate, and the solvent is distilled off. The residue is treated with petroleum benzine and the resulting powder is collected by filtration.

Yield 10.6 g (66.2%), m.p. 74°–77° C., $[\alpha]_D^{23} -81.4°$ (c=0.6, methanol), $Rf^1$ 0.38, $Rf^2$ 0.66

Elemental analysis (for $C_{28}H_{42}O_7N_4$): Calcd. C, 61.52; H, 7.74; N, 10.25; Found C, 61.61; H, 7.94; N, 9.92.

(c) Production of Z-Ile-Leu-Pro-Gln-OBu$^t$:

In 500 ml of methanol is dissolved 10.6 g of Z-Leu-Pro-Gln-OBu$^t$ and catalytic reduction is carried out with palladium black as catalyst. The methanol is distilled off and the residue is dissolved in 300 ml of ethyl acetate. To this solution is added 200 ml of a solution of Z-Ile-ONB (prepared from 5.1 g of Z-Ile-OH, 4.2 g of HONB and 4.4 g of DCC) in ethyl acetate-dioxane (1:1), and the mixture is stirred for 16 hours. The solvent is removed from the reaction mixture by distillation and the residue is dissolved in 400 ml of ethyl acetate. The reaction mixture is washed with 0.2N-HCl, 4% aqueous sodium hydrogen carbonate and water in that order, followed by drying over anhydrous sodium sulfate. The solvent is distilled off, the residue treated with petroleum benzine, and the resulting powder collected by filtration.

Yield 12.1 g (94.5%), m.p. 78°–80° C. (decompn.), $[\alpha]_D^{23} -87.0°$ (c=0.42, methanol), $Rf^1$ 0.23, $Rf^2$ 0.67.

Elemental analysis (for $C_{34}H_{53}O_8N_5$): Calcd. C, 61.89; H, 8.10; N, 10.62; Found C, 62.35; H, 8.31; N, 10.16.

(d) Production of Z-Pro-Ile-Leu-Pro-Gln-OBu$^t$:

In 500 ml of methanol is dissolved 12 g of Z-Ile-Leu-Pro-Gln-OBu$^t$ and catalytic reduction is carried out in hydrogen gas stream using palladium black as catalyst. The catalyst is filtered off and the solvent is distilled off. The residue is dissolved in 100 ml of DMF, 4.7 g of Z-Pro-OH and 3.0 g of HOBt are added, the mixture is cooled to 0° C., and further, 4.3 g of DCC is added. The mixture is stirred at 0° C. for 4 hours and then at room temperature for 10 hours. The precipitate is filtered off, the solvent distilled off and the residue dissolved in 400 ml of ethyl acetate. The solution is washed with 0.2N-HCl, 4% aqueous sodium hydrogen carbonate and water in that order, followed by drying over anhydrous sodium sulfate. The solvent is distilled off, followed by addition of diethyl ether to the residue, and the mixture is warmed. After removal of the supernatant, the residue is treated with diethyl ether and the resulting powder is collected by filtration.

Yield 12.6 g (91.5%), m.p. 83°–87° C. (decompn.) $[\alpha]_D^{23} -121.0°$ (c=0.5, methanol), $Rf^1$ 0.31, $Rf^2$ 0.84.

Elemental analysis (for $C_{39}H_{60}O_9N_6$): Calcd. C, 61.88; H, 7.99; N, 11.10; Found C, 62.04; H, 8.21; N, 10.70.

(e) Production of Z-Thr-Pro-Ile-Leu-Pro-Gln-OBu$^t$:

In 500 ml of methanol is dissolved 12.5 g of Z-Pro-Ile-Leu-Pro-Gln-OBu$^t$ and catalytic reduction is carried out in hydrogen gas stream using palladium black as catalyst. The catalyst is filtered off, the solvent distilled off, and the residue dissolved in 100 ml of DMF. To this solution are dissolved 4.2 g of Z-Thr-OH and 2.7 g of HOBt and the solution is cooled to 0° C. Then 3.7 g of DCC is added and the mixture is stirred at 0° C. for 4 hours and at room temperature for 8 hours. The precipitate is filtered off. After removal of the solvent by distillation, the residue is extracted with 400 ml of ethyl acetate and the extract is washed with 0.2N-HCl, 4% aqueous sodium hydrogen carbonate and water in that order, followed by drying over anhydrous sodium sulfate. The solvent is distilled off, the residue treated with diethyl ether and the resulting powder collected by filtration.

Yield 11.8 g (86.8%), m.p. 101°–105° C., $[\alpha]_D^{23} -124.3°$ (c=0.58, methanol), $Rf^1$ 0.20, $Rf^2$ 0.68.

Elemental analysis (for $C_{43}H_{67}O_{11}N_7$): Calcd. C, 60.19; H, 7.87; N, 11.43; Found C, 59,54; H, 7.91; N, 11.19.

(f) Production of Z-Asp(OBu$^t$)-Thr-Pro-Ile-Leu-Pro-Gln-OBu$^t$:

In 500 ml of methanol is dissolved 11.8 g of Z-Thr-Pro-Ile-Leu-Pro-Gln-OBu$^t$ and catalytic reduction is carried out in hydrogen gas stream using palladium black as catalyst. The catalyst is filtered off, the solvent distilled off, and the residue dissolved in 100 ml of DMF. In this solution are dissolved 4.5 g of Z-Asp(OBu$^t$)-OH and 2.3 g of HOBt, and the solution is cooled to 0° C. Then, 3.2 g of DCC is added, the mixture stirred at 0° C. for 4 hours and at room temperature for 10 hours, the precipitate filtered off, and the solvent distilled off. The residue is treated with 150 ml of ethyl acetate, and the resulting gel-like precipitate is collected by filtration, crystallized from ethyl acetate-diethyl ether, and collected by filtration with diethyl ether.

Yield 12.15 g (85.9%), m.p. 94°–96° C. (decompn.), $[\alpha]_D^{21} -109.1°$ (c=0.59, methanol), $Rf^1$ 0.13, $Rf^2$ 0.47.

Elemental analysis (for $C_{51}H_{80}O_{14}N_8 \cdot H_2O$): Calcd. C, 58.49; H, 7.89; N, 10.70; Found C, 58.60; H, 8.07; N, 10.71.

(g) Production of Z-Ser-Asp(OBu$^t$)-Thr-Pro-Ile-Leu-Pro-Gln-OBu$^t$:

In 500 ml of methanol is dissolved 12 g of Z-Asp(OBu$^t$)-Thr-Pro-Ile-Leu-Pro-Gln-OBu$^t$ and catalytic reduction is carried out in hydrogen gas stream using palladium black as catalyst. The catalyst is filtered off, the solvent distilled off, and the residue dissolved in 100 ml of DMF, together with 2.93 g of Z-Ser-OH and 2.0 g of HOBt. The solution is cooled to 0° C., followed by addition of 2.8 g of DCC, and the mixture is stirred at 0° C. for 4 hours and then at room temperature for 12 hours. The precipitate is filtered off and the solvent is distilled off. The residue is dissolved in 500 ml of ethyl acetate. The solution is washed with 0.2N-HCl, 4% aqueous sodium hydrogen carbonate and water in that order, followed by drying over anhydrous sodium sulfate, and the solvent is distilled off. The residue is treated with ethyl acetate and diethyl ether, and the resulting powder is collected by filtration.

Yield 11.7 g (90.0%), m.p. 111°–115° C. (decompn.), $[\alpha]_D^{21} -112.3°$ (c=0.63, methanol), $Rf^1$ 0.06, $Rf^2$ 0.31.

Elemental analysis (for $C_{54}H_{85}O_{16}N_9 \cdot H_2O$): Calcd. C, 57.17; H, 7.73; N, 11.11; Found C, 57.34; H, 7.77; N, 11.14.

(h) Production of Z-Pro-Ser-Asp(OBu$^t$)-Thr-Pro-Ile-Leu-Pro-Gln-OBu$^t$:

In 500 ml of methanol is dissolved 11.6 g of Z-Ser-Asp(OBu$^t$)-Thr-Pro-Ile-Leu-Pro-Gln-OBu$^t$ and catalytic reduction is carried out in hydrogen gas stream using palladium black as catalyst. The catalyst is filtered off and the solvent distilled off. The residue, together with 4.3 g of Z-Pro-OBN, is dissolved in 100 ml of DMF, and the solution is stirred at room temperature for 16 hours. The solvent is distilled off, the residue is extracted with 500 ml of ethyl acetate, and the extract is washed with 0.2N-HCl, 4% aqueous sodium hydrogen carbonate and water in that order. After drying over anhydrous sodium sulfate, the solvent is distilled off. The residue is treated with diethyl ether and the resulting powder is collected by filtration.

Yield 11.1 g (88.1%), m.p. 117°–120° C., $[\alpha]_D^{21}$ −119.2° (c=0.61, methanol), Rf$^2$ 0.45.

Elemental analysis (for $C_{59}H_{92}O_{17}N_{10} \cdot H_2O$): Calcd. C, 57.54; H, 7.69; N, 11.38; Found C, 57.44; H, 7.69; N, 11.38.

(i) Production of Z-Gly-Pro-Ser-Asp(OBu$^t$)-Thr-Pro-Ile-Leu-Pro-Gln-OBu$^t$:

In 500 ml of methanol is dissolved 10 g of Z-Pro-Ser-Asp(OBu$^t$)-Thr-Pro-Ile-Leu-Pro-Gln-OBu$^t$ and catalytic reduction is carried out in hydrogen gas streams using palladium black as catalyst. The catalyst is filtered off and the solvent distilled off. The residue, together with 4 g of Z-Gly-ONB, is dissolved in 80 ml of DMF, and the mixture is stirred at room temperature for 12 hours. The solvent is distilled off, the residue dissolved in 500 ml of ethyl acetate and the solution washed with 0.2N-HCl, 4% aqueous sodium hydrogen carbonate and water in that order. After drying over anhydrous sodium sulfate, the solvent is distilled off. The residue is dissolved in 180 ml of methanol, followed by addition of 4.5 ml of hydrazine hydrate, the mixture is stirred at room temperature for 16 hours, and the solvent is distilled off. The residue is dissolved in 500 ml of ethyl acetate, the solution is washed with water, followed by drying over anhydrous sodium sulfate, and the solvent is distilled off. The residue is treated with diethyl ether and the resulting powder is collected by filtration.

Yield 7.35 g (70.2%), m.p. 131°–135° C. (decompn.), $[\alpha]_D^{22}$ −119.4° (c=0.35, methanol), Rf$^2$ 0.27.

Elemental analysis (for $C_{61}H_{95}O_{18}N_{11} \cdot H_2O$): Calcd. C, 56.86; H, 7.59; N, 11.96; Found C, 56.65; H, 7.68; N, 12.02.

(j) Production of Z-Leu-Pro-OBu$^t$:

In 800 ml of methanol is dissolved 20.2 g of Z-Pro-OBu$^t$ and catalytic reduction is carried out in hydrogen gas stream using palladium black as catalyst. The catalyst is filtered off and the solvent is distilled off. The residue is dissolved in 300 ml of ethyl acetate, followed by addition of 26.3 g of Z-Leu-OSu, and the mixture is stirred for 16 hours. The reaction mixture is washed with 0.2N-HCl, 4% aqueous sodium hydrogen carbonate and water in that order, followed by drying over anhydrous sodium sulfate, and the solvent is distilled off to give an oily product.

Yield 27.6 g (100%), Rf$^1$ 0.71, Rf$^2$ 0.78.

(k) Production of Z-Arg(NO$_2$)-Leu-Pro-OBu$^t$:

In 500 ml of methanol is dissolved 13.8 g of Z-Leu-Pro-OBu$^t$ and catalytic reduction is carried out in hydrogen gas stream using palladium black as catalyst. The catalyst is filtered off and the solvent distilled off. The residue, together with 11.7 g of Z-Arg(NO$_2$)-OH and 6.7 g of NOBt, is dissolved in 200 ml of DMF and the solution is cooled to 0° C. Then, 7.5 g of DCC is added, the mixture stirred at 0° C. for 4 hours and then at room temperature for 12 hours, the precipitate filtered off, and the solvent distilled off. The residue is extracted with 600 ml of ethyl acetate, the extract washed with 0.2N-HCl, 4% aqueous sodium hydrogen carbonate and water in that order, followed by drying over anhydrous sodium sulfate, and the solvent is distilled off. The residue is allowed to stand and the resulting crystals are treated with diethyl ether. The residue is collected by filtration, and recrystallized from methanol.

Yield 12.4 g (60.6%), m.p. 170°–172° C., $[\alpha]_D^{26}$ −67.8° (c=0.48, methanol), Rf$^3$ 0.77.

Elemental analysis (for $C_{29}H_{45}O_8N_7$): Calcd. C, 56.20; H, 7.32; N, 15.82; Found C, 55.79; H, 7.16; N, 15.85.

(l) Production of Z-Ser-Arg-Leu-Pro-OBu$^t$:

In 500 ml of methanol is dissolved 12.3 g of Z-Arg(NO$_2$)-Leu-Pro-OBu$^t$, followed by addition of 6.6 ml of 6N-NCl, and catalytic reduction is carried out in hydrogen gas stream using palladium black as catalyst. The catalyst is filtered off and the solvent distilled off. The residue, together with 2.8 ml of triethylamine, is dissolved in 100 ml of DMF, and the triethylamine hydrochloride is filtered off. To the filtrate are added 4.8 g of Z-Ser-OH and 5.4 g of HONB and the mixture is cooled to 0° C. Then, 4.95 g of DCC is added, and the mixture is stirred at 0° C. for 4 hours and at room temperature for 16 hours. The precipitate is filtered off, the solvent distilled off, and the residue extracted with 500 ml of ethyl acetate. The extract is washed well with saturated aqueous sodium chloride, followed by drying over anhydrous sodium sulfate, and the solvent is distilled off to give a syrupy residue. Rf$^3$ 0.53

(m) Production of Z-Pro-Ser-Arg-Leu-Pro-OBu$^t$:

In 500 ml of methanol are dissolved 10.5 g of Z-Ser-Arg-Leu-Pro-OBu$^t$ and 3 ml of 6N-HCl and catalytic reduction is carried out in hydrogen gas stream using palladium black as catalyst. The catalyst is filtered off, the solvent distilled off, the residue dissolved in 100 ml of DMF, and the solution neutralized with 2.52 ml of triethylamine. The triethylamine hydrochloride is filtered off, followed by addition of 8.4 g of Z-Pro-ONB, and the mixture is stirred at room temperature for 16 hours. The solvent is distilled off, 300 ml of ethyl acetate and 300 ml of saturated aqueous sodium chloride are added to the residue, and the mixture is shaken thoroughly. The reaction mixture is left standing, and oily precipitates are recovered from the aqueous layer, followed by addition of diethyl ether. The resulting powder is dissolved in methanol, the insolubles filtered off, and the solvent distilled off. The residue is further treated with diethyl ether and the resulting powder is collected by filtration.

Yield 8.45 g (70.8%), m.p. 115°–120° C. (decomp.), $[\alpha]_D^{22}$ −84.7° (c=0.53, methanol), Rf$^3$ 0.41.

Elemental analysis (for $C_{37}H_{58}O_9N_8 \cdot HCl \cdot H_2O$): Calcd. C, 54.63; H, 7.56; N, 13.78; Cl, 4.36; Found C, 54.50; H, 7.70; N, 14.11; Cl, 4.21.

(n) Production of Z-Ser-Pro-Ser-Arg-Leu-Pro-OBu$^t$:

In 200 ml of methanol is dissolved 3.8 g of Z-Pro-Ser-Arg-Leu-Pro-OBu$^t$ and catalytic reduction is carried out in hydrogen gas stream using palladium black as catalyst. The catalyst is filtered off, the solvent distilled off, and the residue dissolved in 30 ml of DMF. To this solution is added a solution (10 ml) of Z-Ser-ONB (prepared from 1.37 g of Z-Ser-OH, 1.24 g HONB and 1.30 g of DCC) in DMF, and the mixture is stirred at room temperature for 16 hours. The precipitate is filtered off and the solvent is distilled off. The residue is dissolved by the addition of 1 ml ethyl acetate and 1 ml of acetonitrile, then the solution is treated with ether, and the resultant powder is recovered by filtration. This powder is further dissolved in 2 ml of a 1:1 mixture of solvent $Rf^3$ and ethyl acetate, applied to a column (5.6×9.0 cm) packed with silica gel using the same solvent and developed with the same solvent. Fractions from 365 ml of 746 ml are pooled, the solvent distilled off, the residue treated with diethyl ether and the resultant powder collected by filtration.

Yield 2.12 g (50.2%), m.p. 130°–135° C. (decomp.), $[\alpha]_D^{22}$ −83.5° (c=0.38, methanol), $Rf^3$ 0.34.

Elemental analysis (for $C_{40}H_{63}O_{11}N_9 \cdot HCl \cdot H_2O$): Calcd. C, 53.35; H, 7.39; N, 14.00; Cl, 3.94; Found C, 53.67; H, 7.45; N, 13.72; Cl, 3.52.

(o) Production of Z-Ser-Leu-Pro-OBu$^t$:

In 700 ml of methanol is dissolved 13.8 g of Z-Leu-Pro-OBu$^t$ and catalytic reduction is carried out in hydrogen gas stream using palladium black as catalyst. The catalyst is filtered off and the solvent distilled off. The residue, together with 7.9 g of Z-Ser-OH and 8.9 g of HONB, is dissolved in 200 ml of acetonitrile and the solution is cooled to 0° C. Then, 7.5 g of DCC is added and the mixture is stirred at 0° C. for 4 hours and at room temperature for 16 hours. The precipitate is filtered off, the solvent distilled off, and the residue extracted with 500 ml of ethyl acetate. The extract is washed with 0.2N-HCl, 4% aqueous sodium hydrogen carbonate and water in that order, followed by drying over anhydrous sodium sulfate, and the solvent is distilled off to give 17 g of oil. This oil is dissolved in 15 ml of chloroform-methanol (200:3) and applied to a column (5.4×20 cm) packed with silica gel using the same solvent and developed with the same solvent. Fractions from 1300 to 2100 ml are pooled and the solvent is distilled off to give an oily product.

Yield 12.2 g (73.1%), $Rf^1$ 0.38, $Rf^2$ 0.69.

(p) Production of Z-Ser-Leu-Pro-Ser-Pro-Ser-Arg-Leu-Pro-OBu$^t$:

In 60 ml of methanol are dissolved 1.0 g of Z-Ser-Pro-Ser-Arg-Leu-Pro-OBu$^t$ and 1.2 ml of 1N-HCl, and catalytic reduction is carried out in hydrogen gas stream using palladium black as catalyst. The catalyst is filtered off, the solvent distilled off, and the residue dissolved in 20 ml of DMF. In 7 ml of trifluoroacetic acid is dissolved 700 mg of Z-Ser-Leu-Pro-OBu$^t$ and, after 50 minutes, the solvent is distilled off. The residue is washed with a mixture of diethyl ether-petroleum ether (1:2), the washings are discarded and the oily residue is dried under reduced pressure of a vacuum pump to give a powder. The powder is immediately dissolved in the above DMF solution together with 407 mg of HONB. Then, at 0° C., 466 mg of DCC is added and the mixture stirred at 0° C. for 6 hours and then at room temperature for 16 hours. The precipitate is filtered off and the solvent distilled off. The residue is dissolved in 5 ml of solvent $Rf^3$-ethyl acetate (4:1), applied to a column (3.6×9.0 cm) packed with silica gel using the same solvent and eluted with the same solvent. Fractions from 333 to 572 ml are pooled, the solvent distilled off, the residue treated with diethyl ether, and the resulting powder is collected by filtration.

Yield 450 mg (33.8%), m.p. 110°–120° C. (decomp.), $[\alpha]_D^{24}$ −106.6° (c=0.31, methanol), $Rf^5$ 0.71.

(q) Production of Z-Pro-Pro-OBu$^t$:

In 500 ml of methanol is dissolved 10.1 g of Z-Pro-OBu$^t$ and catalytic reduction is carried out in hydrogen gas stream using palladium black as catalyst. The catalyst is filtered off and the solvent distilled off. The residue, together with 8.47 g of Z-Pro-OH and 5.4 g of HOBt, is dissolved in 300 ml of ethyl acetate, and the solution is cooled to 0° C. Then, 7.5 g of DCC is added, the mixture is stirred at 0° C. for 4 hours and then at room temperature for 12 hours, and the precipitate is filtered off. The filtrate is washed with 0.2N-HCl, 4% aqueous sodium hydrogen carbonate and water in that order, followed by drying over anhydrous sodium sulfate, and the solvent is distilled off. The crystalline residue is treated with diethyl ether and collected by filtration.

Yield 9.85 g (74.1%), m.p. 94°–96° C., $[\alpha]_D^{22}$ −116.9° (c=0.54, methanol), $Rf^1$ 0.58, $Rf^2$ 0.72.

Elemental analysis (for $C_{22}H_{30}O_5N_2$): Calcd. C, 65.65; H, 7.51; N, 6.96; Found C, 65.42; H, 7.38; N, 7.20.

(r) Production of Z-Pro-Pro-Pro-OBu$^t$:

In 300 ml of methanol is dissolved 9 g of Z-Pro-Pro-OBu$^t$ and catalytic reduction is carried out in hydrogen gas stream using palladium black as catalyst. The catalyst is filtered off and the solvent distilled off. The residue, together with 5.6 g of Z-Pro-OH and 3.63 g of HOBt, is dissolved in 250 ml of ethyl acetate and the solution is cooled to 0° C. Then, 5.1 g of DCC is added, and the mixture is stirred at 0° C. for 6 hours and at room temperature for 16 hours. The precipitate is filtered off. The filtrate is washed with 0.2N-HCl, 4% aqueous sodium hydrogen carbonate and water in that order, followed by drying over anhydrous sodium sulfate, and the solvent is distilled off. The crystalline residue is treated with diethyl ether and filtered.

Yield 9.6 g (85.9%), m.p. 135°–157° C., $[\alpha]_D^{22}$ −176.0° (c=0.55, methanol), $Rf^1$ 0.40, $Rf^2$ 0.69

Elemental analysis (for $C_{27}H_{37}O_6N_3 \cdot \frac{1}{2}H_2O$): Calcd. C, 63.76; H, 7.53; N, 8.26; Found C, 63.77; H, 7.53; N, 8.62.

(s) Production of Z-Ala-Pro-Pro-Pro-OBu$^t$:

In 200 ml of methanol is dissolved 5 g of Z-Pro-Pro-Pro-OBu$^t$ and catalytic reduction is carried out in hydrogen gas stream using palladium black as catalyst. The catalyst is filtered off and the solvent distilled off. The residue, together with 2.23 g of Z-Ala-OH and 1.62 g of HOBt, is dissolved in 20 ml of DMF and the solution is cooled to 0° C. To this solution is added 2.27 g of DCC, and the mixture is stirred at 0° C. for 4 hours and then at room temperature for 12 hours. The precipitate is filtered off and the solvent distilled off. The residue is dissolved in 3 ml of 2% methanol-chloroform, applied to a column (3.7×10.5 cm) packed with silica gel using said solvent, and developed with said solvent. Fractions from 170 to 380 ml are pooled and the solvent is distilled off to give 4.05 g (71.0%) of oily product. $Rf^1$ 0.33, $Rf^2$ 0.67.

(t) Production of Z-Ala-Pro-Pro-Pro-Ser-Leu-Pro-Ser-Pro-Ser-Arg-Leu-Pro-OBu$^t$:

In 80 ml of methanol is dissolved 400 mg of Z-Ser-Leu-Pro-Ser-Pro-Ser-Arg-Leu-Pro-OBu$^t$ together with 0.8 ml of 1N-HCl, and catalytic reduction is carried out in hydrogen gas stream using palladium black as catalyst. The catalyst is filtered off and the solvent is distilled off. The residue is dissolved in 10 ml of DMF, the solution neutralized with 0.11 ml of triethylamine, and the triethylamine hydrochloride is filtered off. In 2 ml of trifluoroacetic acid is dissolved 233 mg of Z-Ala-Pro-Pro-Pro-OBu$^t$ and, after 50 minutes, the solvent is distilled off. To the residue is added diethyl ether and the resulting powder is collected by filtration and dried. The powder, together with 122 mg of HONB, is dissolved in the above DMF solution and the solution is cooled to 0° C. To this solution is added 140 mg of DCC, the mixture is stirred at 0° C. for 6 hours and then at room temperature for 12 hours. The precipitate is removed by filtration, and the solvent distilled off. To the residue is added diethyl ether and the resulting powder is collected by filtration and recrystallized from acetonitrile and ethyl acetate.

Yield 430 mg (82.1%), m.p. 152°–155° C. (decomp.), $[\alpha]_D^{24} - 153.6°$ (c=0.45, methanol), Rf$^3$ 0.10, Rf$^5$ 0.54.

Elemental analysis (for $C_{72}H_{112}O_{19}N_{16}\cdot HCl\cdot H_2O$): Calcd. C, 55.42; H, 7.43; N, 14.37; Cl, 2.27; Found C, 56.21; H, 7.54; N, 14.04; Cl, 2.30.

(u) Production of Z-Ala-Pro-Pro-Pro-Ser-Leu-Pro-Ser-Pro-Ser-Arg-Leu-Pro-Gly-Pro-Ser-Asp(OBu$^t$)-Thr-Pro-Ile-Leu-Pro-Gln-OBu$^t$ In 30 ml of methanol is dissolved 363 mg of Z-Gly-Pro-Ser-Asp(OBu$^t$)-Thr-Pro-Ile-Leu-Pro-Gln-OBu$^t$ and catalytic reduction is carried out in hydrogen gas stream using palladium black as catalyst. The catalyst is filtered off, the solvent distilled off, and the residue dissolved in 10 ml of DMF. In 3 ml of trifluoroacetic acid is dissolved 430 mg of Z-Ala-Pro-Pro-Pro-Ser-Leu-Pro-Ser-Pro-Ser-Arg-Leu-Pro-OBu$^t$ and the solution is allowed to stand at room temperature for 45 minutes. The solvent is distilled off, the residue treated with diethyl ether, and the resulting powder collected by filtration and dried. The powder, together with 103 mg of HONB, is dissolved in the above DMF solution and the mixed solution is cooled to 0° C. Then, 118 mg of DCC is added and the mixture is stirred at 0° C. for 6 hours and then at room temperature for 40 hours. The precipitate is filtered off and the solvent distilled off. The residue is treated with diethyl ether and the resulting powder is collected by filtration and further reprecipitated from DMF and diethyl ether.

Yield 700 mg (95.5%), m.p. 120°–125° C. (decomp.), $[\alpha]_D^{23} - 127.7°$ (c=0.12, methanol), Rf$^5$ 0.62, Rf$^6$ 0.44.

Elemental analysis (for $C_{121}H_{191}O_{34}N_{27}\cdot HCl\cdot 2H_2O$): Calcd. C, 53.12; H, 7.80; N, 14.94; Cl 1.40; Found C, 53.39; H, 7.62; N, 15.10; Cl, 1.54.

(v) Production of H-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln-OH [peptide (I)][the C-terminal fragment peptide of hCG-β (123–145)]

In 50 ml of methanol are dissolved 580 mg of Z-Ala-Pro-Pro-Pro-Ser-Leu-Pro-Ser-Pro-Ser-Arg-Leu-Pro-Gly-Pro-Ser-Asp(OBu$^t$)-Thr-Pro-Ile-Leu-Pro-Gln-OBu$^t$ and 0.45 ml of 1N-HCl, and catalytic reduction is carried out in hydrogen gas stream using palladium black as catalyst. The catalyst is removed by filtration, the solvent distilled off and 1 ml of water is added to the residue, followed by redistillation. The residue is dissolved in 10 ml of 90% aqueous trifluoroacetic acid and allowed to stand at room temperature for 60 minutes. After the solvent is distilled off, the residue is dissolved by addition of 10 ml of water and subjected to column chromatography on Amberlite IRA-410 (acetate-form; column size 1×5 cm). The eluate is collected. The resin is washed well with 50 ml of water and the washings are combined with the eluate and lyophilized to obtain 390 mg of a white powder. This powder is applied to a column (2×83 cm) of Sephadex LH-20 packed with 1N-acetic acid, and developed with the same solvent. Fractions from 70 to 100 ml are pooled, lyophilized and rechromatographed in the manner as above, using said developing solvent. The fractions containing the desired compound are pooled and lyophilized to give white powder.

Yield 185 mg (35.2%), $[\alpha]_{D4}^{23} - 194.5°$ (c=0.13, 0.1N-acetic acid), Rf$^5$ 0.06, Rf (cellulose) 0.78.

Amino acid analysis (calcd.): Arg 1.00(1), Asp 1.00(1), Thr 1.00(1), Ser 3.74(4), Glu 1.03(1), Pro 9.59(9), Gly 0.98(1), Ala 0.94(1), Ile 0.95(1), Leu 2.97(3). Average recovery rate: 79.3%.

REFERENCE EXAMPLE 2

Production of H-Ser-Pro-Ser-Arg-Leu-Pro-Gly-Pro-Ser-Asp-Thr-Pro-Ile-Leu-Pro-Gln-OH [hereinafter referred to as peptide (II)][the C-terminal fragment peptide of hCG-β (130–145)]:

In 100 ml of methanol is dissolved 2.16 g of Z-Gly-Pro-Ser-Asp(OBu$^t$)-Thr-Pro-Ile-Leu-Pro-Gln-OBu$^t$ and catalytic reduction is carried out in hydrogen gas stream using palladium black as catalyst. The catalyst is filtered off, the solvent distilled off and the residue is dissolved in 25 ml of DMF. To this solution is added Z-Ser-Pro-Ser-Arg-Leu-Pro-OH, which has been obtained by treating 1.5 g of Z-Ser-Pro-Ser-Arg-Leu-Pro-OBu$^t$ with trifluoroacetic acid, as well as 1.22 g of HONB, followed by cooling to 0° C. Then, 701 mg of DCC is added and the mixture is stirred at 0° C. for 6 hours and at room temperature for 40 hours. The precipitate is removed by filtration and the solvent is distilled off. The residue is precipitated with ethyl acetate and diethyl ether and filtered. The precipitate is dissolved in 5 ml of solvent Rf$^3$, applied to a silica gel column (5.7×9 cm) packed with said solvent and developed also with said solvent. Fractions from 534 to 914 ml are pooled, distilled to remove the solvent, precipitated with diethyl ether and filtered.

Yield 1.1 g (33.9%), Rf$^3$ 0.20.

Then, a 70 mg portion of the above protected peptide is dissolved in 10 ml of methanol and catalytic reduction is carried out in hydrogen gas stream using palladium black as catalyst. The catalyst is filtered off and the solvent distilled off. The residue is dissolved in 1 ml of 90% trifluoroacetic acid, and after 60 minutes, the solvent is distilled off. The residue is dissolved by the addition of 3 ml of water and subjected to column chromatography on Amberlite IRA-410 (acetate-form; column size 1×1 cm), followed by lyophilization. Then, the lyophilizate is dissolved in 0.5 ml of 1N-acetic acid, applied to a column of Sephadex LH-20 packed with 1N-acetic acid, and developed with said solvent. The fractions containing the desired compound are pooled and lyophilized to give white powder.

Yield 22 mg (36.1%), $[\alpha]_D^{23} - 159.3°$ (c=0.15, 0.1N-acetic acid), Rf$^5$ 0.15.

Amino acid analysis (calcd.): Arg 1.01(1), Asp 1.01(1), Thr 0.98(1), Ser 2.57(3), Glu 0.96(1), Pro 4.85(5), Gly 1.00(1), Ile 0.96(1), Leu 2.04(2), average recovery rate: 81.1%.

REFERENCE EXAMPLE 3

Production of H-Gly-Pro-Ser-Asp-Thr-Pro-Ile-Leu-Pro-Gln-OH [hereinafter referred to as peptide (III)][the C-terminal fragment peptide of hCG-β (136–145)]:

In 2.5 ml of 90% trifluoroacetic acid is dissolved 150 mg of Z-Gly-Pro-Ser-Asp(OBu$^t$)-Thr-Pro-Ile-Leu-Pro- Gln-OBu$^t$ and the solution is allowed to stand at room temperature for 60 minutes. Then, the solvent is distilled off, the residue is dissolved in 30 ml of 50% acetic acid, and catalytic reduction is carried out in hydrogen gas stream using palladium black as catalyst. The catalyst is filtered off and the solvent is distilled off. The residue is dissolved in 10 ml of water, subjected to column chromatography on Amberlite IRA-410 (acetate-form; column size 1×3 cm), and the resin is washed well with water. The eluate and washings are combined and lyophilized. The lyophilizate is applied to a column (2×83 cm) of Sephadex LH-20 packed with 1N-acetic acid, and developed with said solvent. Fractions from 90 to 105 ml are pooled and lyophilized to give white powder.

Yield 70 mg (57.9%), $[\alpha]_D^{19} -150.5°$ (c=0.2, 0.1N-acetic acid), Rf$^5$ 0.29, Rf$^4$ (cellulose) 0.55.

Amino acid analysis: Asp 1.02(1), Thr 0.98(1), Ser 0.92(1), Glu 1.04(1), Pro 3.17(3), Gly 0.99(1), Ile 0.99(1), Leu 1.00(1). Average recovery rate: 82.6%.

REFERENCE EXAMPLE 4

Production of anti-hCG antibody:

In 1 ml of physiological saline was dissolved 1 mg of hCG (approx. 10,000 IU/mg) purified from human urine by the conventional method, and 1 ml of Freund's complete adjuvant [Tachibana et al: Men-eki-no-Seikagaku (Biochemistry of immunity), p. 26, Kyoritsu Shuppan Inc. Japan (1967)] was added and stirred well to prepare an emulsion. This emulsion was injected into the bilateral femoral muscles and subcutaneously at several dorsal sites of a rabbit. The above procedure was repeated at intervals of 3 weeks for a total of 5 times and a blood sample was taken one week after the last immunization for a pilot assay. In this manner, there was obtained an anti-hCG antibody having a strong affinity for the C-terminal fragment peptide (I), (II) and (III) of hCG-$\beta$.

REFERENCE EXAMPLE 5

Production of specific anti-hCG antibody:

Five (5) mg of peptide (I) obtained in Reference Example 1 was dissolved in 8 ml of 0.1M NaHCO$_3$ containing 0.5M NaCl. To this solution was added 1 g of BrCN-activated Sepharose 4B (Pharmacia Fine Chemicals) previously washed with 1/1,000N-HCl. The mixture was stirred at 5° C. overnight. Then, the Sepharose was washed well with the 0.1M NaHCO$_3$ solution containing 0.5M NaCl as used above, followed by addition of 10 ml of 0.5M ethanolamine adjusted to pH 8 with hydrochloric acid. The reaction was conducted at room temperature for one hour, after which time the Sepharose was washed with (1) 0.1M acetate buffer containing 1M NaCl (pH 4.0), (2) 0.1M borate buffer containing 1M NaCl (pH 8.0) and (3) 0.02M borate buffer containing 0.15M NaCl (pH 8.0) in the order mentioned. The Sepharose was then packed into a column.

Eight (8) ml of the anti-hCG serum obtained according to Reference Example 4 was subjected to fractional precipitation with 1.5 g of anhydrous sodium sulfate and the resultant $\gamma$-globulin fraction was passed through the above column of peptide (I)-Sepharose 4B (column size: 0.9×4 cm).

The column was washed with 0.02M borate buffer containing 0.15M NaCl (pH 8.0) to remove the anti-hCG antibodies showing cross-reactivity with hLH, hFSH and hTSH. Then, elution was carried out with 0.17M glycine-HCl buffer (pH 2.3) to recover the specific anti-hCG antibody having a strong affinity for the C-terminal fragment peptide of hCG-$\beta$. (Protein content 1.8 mg).

The physical properties of the specific antibody thus obtained are as follows.

(1) At the final dilution of 80 ng/ml, this antibody is capable of binding about 95% of the hCG-labeling enzyme conjugate having about 2 $\mu$U of enzymatic activity.

(2) The optimal pH range of the antigen-binding activity of this antibody is 6 to 9.

(3) When stored under refrigerator storage conditions, this antibody remains stable for more than one year.

(4) This antibody has a molecular weight of about 150 thousand and contains about 3% of sugar.

(5) It is readily soluble in aqueous medium between pH 2 and pH 12.

(6) Its electrophoretic behavior belongs to that of the $\gamma$-globulin fraction, showing a migration toward the cathode.

Figure 1:
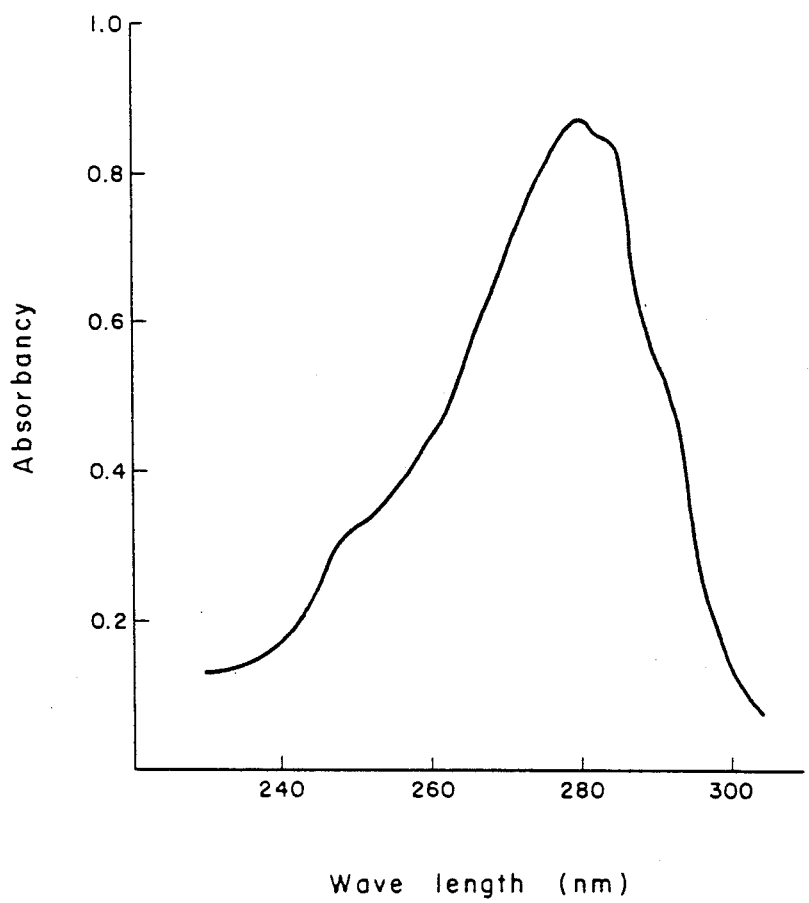
FIG. 1 is an ultraviolet absorption spectrum of a specific anti-hCG antibody obtained in the present invention.

(7) FIG. 1 is ultraviolet absorption spectrum of the specific antibody (the absorption max: about 280 nm).

(8) The amino acid analysis of this antibody is shown in Table 1.

(9) Other properties of this antibody are identical with those of immunoglobulin G [Kikuchi et al: Ika Meneki Gaku (Medical Immunology), p. 61, Nankodo Inc. Japan (1976)].

TABLE 1

| Amino acid | The number of moles of each amino acid of antibody per 100 moles of glycine. |
|---|---|
| Lys | 94 |
| His | 40 |
| Arg | 41 |
| Asp | 114 |
| Thr | 103 |
| Ser | 126 |
| Glu | 142 |
| Pro | 103 |
| Gly | 100 |
| Ala | 77 |
| Val | 134 |
| Met | 3 |
| Ile | 33 |
| Leu | 109 |
| Tyr | 40 |
| Phe | 59 |

EXAMPLE 1

(1) Production of anti-hCG-$\beta$ C-terminal fragment peptide antibody:

In 4 ml of 0.2M phosphate buffer (pH 7.3) are dissolved 25 mg of the peptide (I) prepared in Reference Example 1 [hCG-$\beta$(123–145) C-terminal peptide moiety] and 50 mg of bovine thyroglobulin (briefly, BTG), followed by addition of 4 ml of 5% aqueous GLA. The mixture is stirred at room temperature for 3 hours, after which it is dialyzed against water at 4° C. (2 l of water×4) and lyophilized to obtain an inoculum. In 0.75 ml of physiological saline is dissolved 1.5 mg of the above hCG-$\beta$ C-terminal peptide (123–145)-BTG conjugate, followed by addition of 0.75 ml of Freund's complete adjuvant. The mixture is stirred well to prepare an emulsion. The emulsion was injected intramuscularly into bilateral femurs and subcutaneously in the back of a rabbit. The above procedure is repeated four times at intervals of 4 weeks and the blood was withdrawn a week after the last immunization, centrifuged to separate the antiserum. In the above manner, anti-hCG-β C-terminal peptide(123–145) serum F5C is obtained.

This antiserum F5C is precipitated with ammonium sulfate in the conventional manner and the resulting γ-globulin fraction is applied to a Sepharose 4B column supporting 2 mg of hCG (0.9 cm dia.×4 cm long).

The column is washed with 0.02M borate buffer containing 0.15M NaCl (pH 8.0) and elution is carried out with 0.17M glycine-HCl buffer (pH 2.3), whereby a specific antibody F5CS having a high affinity for hCG is obtained.

(2) Production of an antibody-carrying solid phase:

To 300 polystyrene balls (6.4 mm in dia., Precision Plastic Ball Co., Chicago, U.S.A.) is added 50 ml of 0.01M phosphate buffer (pH 7.7) and the system is heated to 56° C. Then, 2 mg of the F5CS prepared above in (1) is added and the system is incubated at 56° C. for 2 hours. The balls are washed with 0.05M phosphate buffer (pH 7.0) containing 0.1% BSA and stored in a refrigerator till use.

(3) Production of β-D-galactosidase-labeled anti-hCG antibody conjugate:

A rabbit is immunized with 1 mg of about 10,000 IU/mg of hCG as purified from human urine in the conventional manner and the resultant anti-hCG serum is subjected to fractional precipitation (salting-out) with ammonium sulfate and affinity chromatography on a Sepharose 4B column carrying 5 mg of peptide (I) (column dia. 0.9 cm, length 4 cm). The effluent from the column is used as antibody T7CS. In 2 ml of 0.05M phosphate buffer (pH 7.0) is dissolved 4 mg of the above antibody T7CS, and the solution is reacted with 200 μl of THF containing 400 μg of m-MBHS at 30° C. for 30 minutes. The reaction mixture is passed through a Sephadex G-25 column (0.9 cm dia., 55 cm long) equilibrated with 0.02M phosphate buffer to separate the excess reagent from the maleimidated antibody. 0.5 ml of the maleimidated antibody is gradually added to 0.3 ml of a β-D-galactosidase solution (1 mg/ml) diluted with 0.02M phosphate-NaCl buffer (pH 7.5) and the mixture is reacted at 5° C. overnight with occasional shaking. After the reaction is completed, the mixture is purified by Sepharose 6B column chromatography with 0.02M phosphate-NaCl buffer (pH 7.0) and fraction containing both enzymatic activity and antibody activity is collected. The above procedure yielded a β-D-galactosidase-labeled anti-hCG antibody conjugate.

Figure 2:
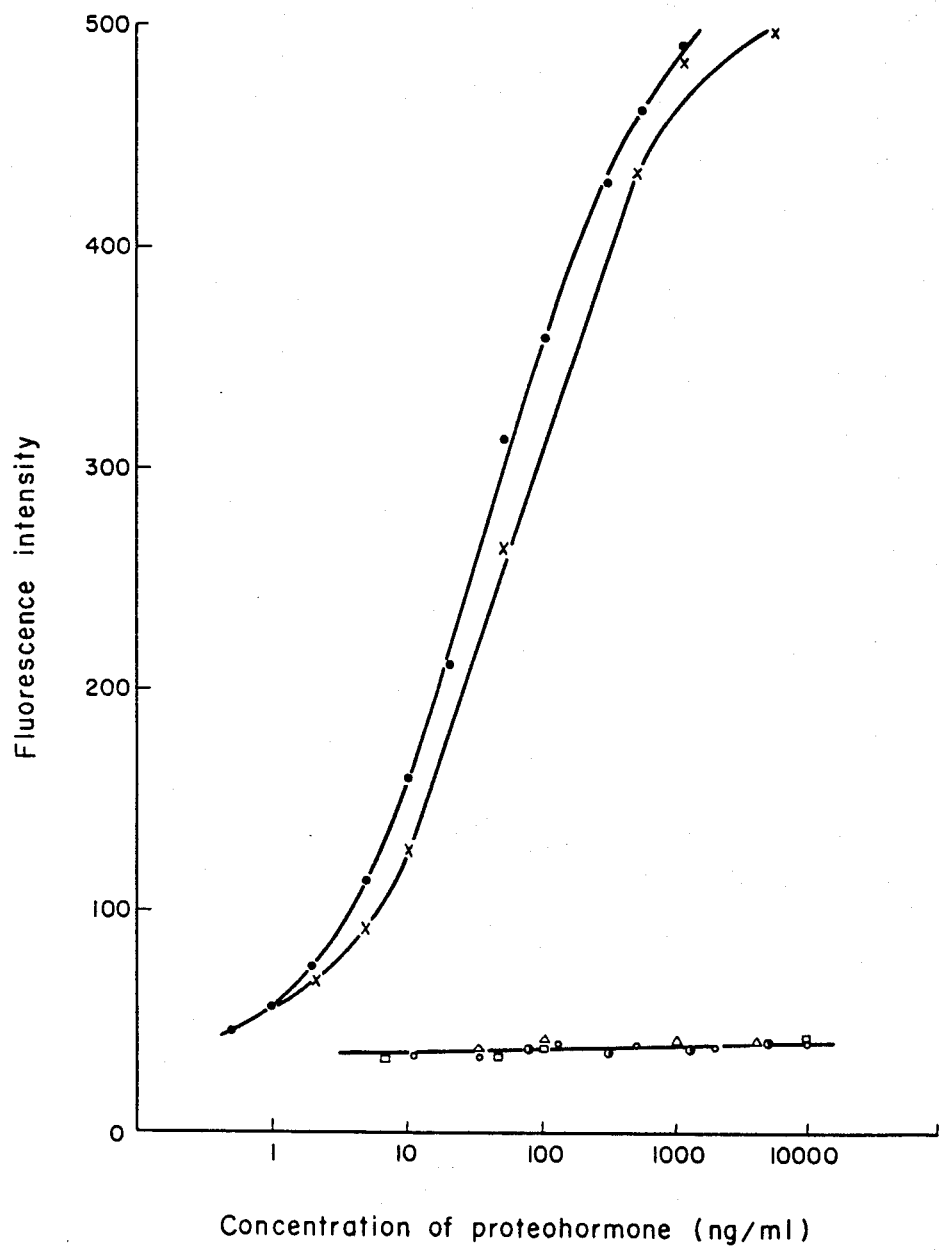
FIGS. 2 and 3 show standard curves for various proteohormones.

(4) Assay:

To 400 μl of 0.1M phosphate buffer containing 5% of normal rabbit serum, 0.1% of NaN₃ and 1 mM of MgCl₂ is added 100 μl of the standard solution of hCG, hCG-α, hCG-β, hLH, hFSH or hTSH, and one ball of the anti-hCG-β C-terminal peptide(123–145) antibody-carrying polystyrene prepared above in (2) and 100 μl of the β-D-galactosidase-labeld anti-hCG antibody solution prepared above in (3) are added. The mixture is reacted at room temperature for 2 hours. After the reaction, the polystyrene ball is washed three times with 0.05M phosphate buffer containing 0.1M of NaCl and 1 mM of MgCl₂. To the ball is added 400 μl of an enzyme substrate solution [a 20 μg/ml solution of 4-methylumbelliferyl-β-D-galactopyranoside in 0.02M phosphate buffer (pH 7.0) containing 0.1% bovine serum albumin, 0.1% NaN₃, 0.1M NaCl and 1 mM MgCl₂] and the reaction is conducted at 37° C. for 2 hours. The fluorescence intensity is measured at 450 nm with an excitation wavelength of 365 nm. The standard curves are shown in FIG. 2. In FIG. 2, denotes the standard curve of hCG, x the curve of hCG-β, □ the curve of hCG-α, the curve of hLH, Δ the curve of hFSH and the curve of hTSH.

Thus, the assay method of this invention is specific to hCG and hCG-β only and does not show cross-reactivity with any of hCG-α, hLH, hFSH and hTSH.

EXAMPLE 2

(1) Production of an alkaline phosphatase-labeled anti-hCG antibody conjugate:

In 1 ml of a solution of alkaline phosphatase diluted with 0.1M phosphate buffer (pH 6.8) (0.5 mg/ml) is dissolved 2 mg of the anti-hCG antibody (T7CS) obtained in Example 1 (3), followed by addition of 0.1 ml of 2% GLA. The mixture is reacted at room temperature for 60 minutes. The reaction mixture is dialyzed against 0.02M phosphate-NaCl buffer (pH 6.8) overnight and, then, fractionated on a Sephadex G-200 column to give an alkali phosphatase-labeled anti-hCG antibody conjugate.

(2) Assay:

To 400 ||1 of 0.1M phosphate buffer containing 5% of normal rabbit serum, 0.1% of NaN₃ and 0.1M of NaCl is added 100 μl of the standard solution of hCG, hCG-α, hCG-β, hLH, hFSH or hTSH, followed by addition of one ball of the anti-hCG-β C-terminal peptide(123–145)-antibody prepared in Example 1 (2). The mixture is reacted at room temperature for an hour. The polystyrene ball is washed with 0.1M phosphate buffer and, then, reacted with 100 μl of the alkalinephosphatase-labeled anti-hCG antibody solution prepared above in Example 2 (1) at room temperature for an hour. After the reaction, the polystyrene ball is washed with phosphate buffer and, then, reacted with 100 μl of the substrate solution [a 2 mg/ml solution of p-nitrophenyl phosphate in 0.05M carbonate buffer (pH 9.8) containing 1 mM of MgCl₂] at 37° C. overnight. After the reaction is completed, the absorption intensity of p-nitrophenol is measured at 405 nm and the standard curve is constructed. The same relation as FIG. 2 is thus obtained. The above method is specific to hCG and hCG-β only and shows no cross-reactivity with any of hCG-α, hLH, hFSH and hTSH.

EXAMPLE 3

(1) Preparation of an $^{131}$I-labeled anti-hCG antibody:

To 1.5 mCi of Na$^{131}$I is added 20 μl of 0.25M phosphate buffer (pH 7.5), and a solution of 10 μg of the anti-hCG antibody obtained in Example 1 (3) in 20 μl of phosphate buffer is added, followed by addition of 20 μg of chloramine T in 20 μl of phosphate buffer. The mixture is shaken at room temperature for 30 seconds, after which a solution of 120 μg of sodium metabisulfite in 50 μl of phosphate buffer is promptly added. After addition of 0.4 ml of potassium iodide (10 mg/ml), the reaction mixture is purified on Sephadex G-75 to give $^{131}$I-labeled anti-hCG antibody.

(2) Assay:

To 400 μl of 0.1M phosphate buffer containing 5% of normal rabbit serum, 0.1% of NaN₃ and 0.1M of NaCl is added 100 μl of the standard solution of hCG, hCG-α, hCG-β, hLH, hFSH or hTSH. Then, one ball of the anti-hCG-β C-terminal peptide(123–145) antibody-carrying polystyrene prepared in Example 1 (2) and 100 μl of the iodine-labeled anti-hCG solution prepared in Example 3 (1) are added. The mixture is reacted at room temperature for 2 hours. After the reaction is completed, the polystyrene ball is washed with 0.05M phosphate buffer containing 0.15M NaCl, then, transferred into another test tube, and its radioactivity is measured with a well counter to obtain the standard curve. The same relation as FIG. 2 is obtained. This assay is specific to hCG and hCG-β only and showed no cross-reactivity with hCG-α, hLH, hFSH and hTSH.

EXAMPLE 4

(1) Production of β-D-galactosidase-labeled anti-hCG-α antibody conjugate:

In the same manner as Example 1 (1), the rabbit is immunized with 100 μg of hCG-α [Boehringer Mannheim, Germany] and the resulting anti-hCG-α serum is precipitated with ammonium sulfate and dialyzed against distilled water. The dialysate is subjected to affinity chromatography on a Sepharose 4B column carrying 200 μg of hCG-β [Boehringer Mannheim, Germany] and the effluent is recovered. [This fraction is an anti-hCG-α antibody (F9CS)]. In 2 ml of 0.05M phosphate buffer (pH 7.0) is dissolved 2 mg of the above anti-hCG-α (F9CS), and the solution is treated as in Example 1 (3) to give a β-D-galactosidase-labeled anti-hCG-α antibody conjugate.

Figure 3:
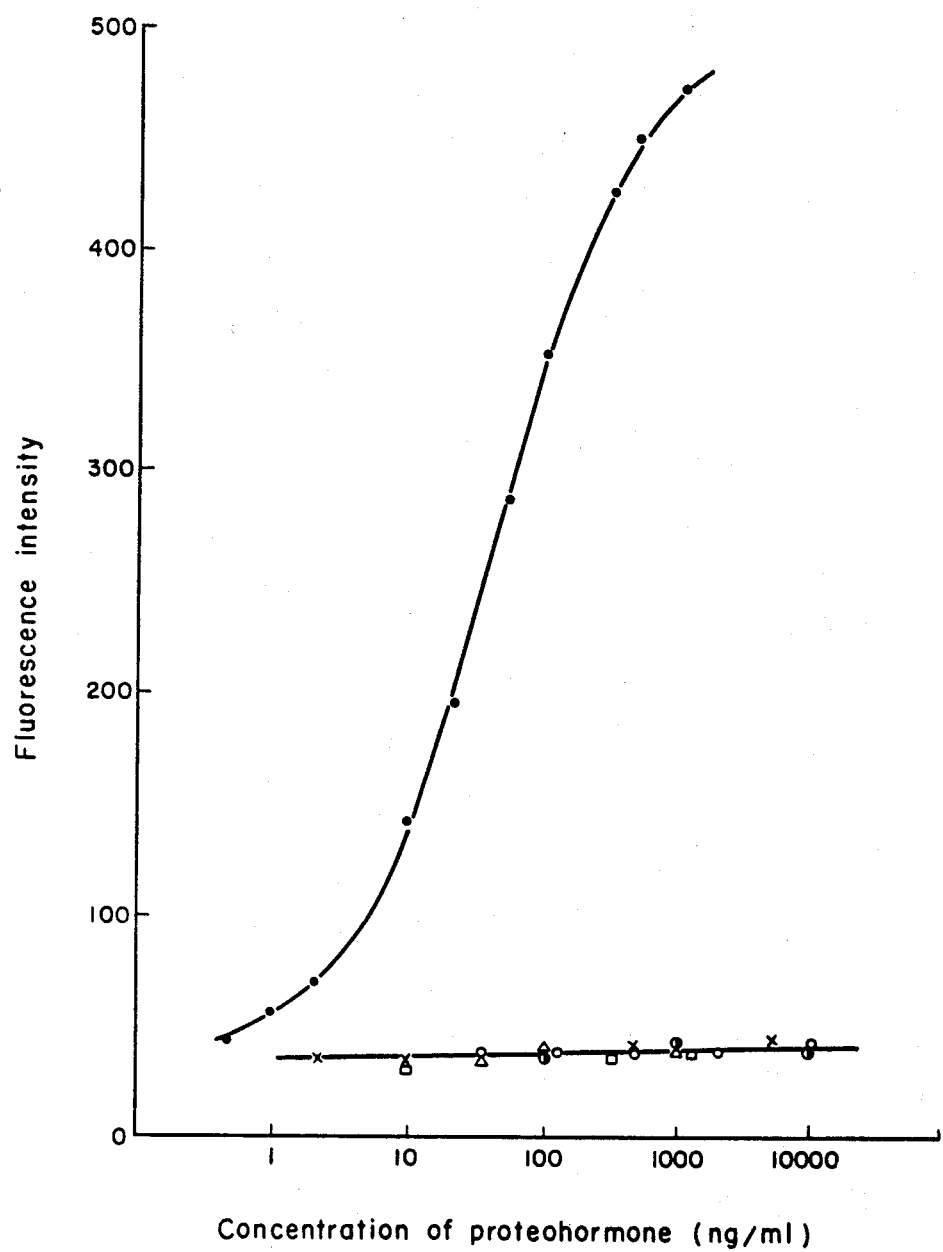

(2) Assay:

To 400 μl of 0.1M phosphate buffer containing 5% of normal rabbit serum, 0.1% of $NaN_3$, 1 mM of $MgCl_2$ and 0.1M of NaCl is added 100 μl of the standard solution of hCG, hCG-α, hCG-β, hLH, hFSH or hTSH, and one ball of the anti-hCG-β C-terminal peptide(1-23-145) antibody-carrying polystyrene prepared in Example 1 (2) and 100 μl of the β-D-galactosidase-labeled anti-hCG-α antibody solution obtained in Example 4 (1) are added. The mixture is reacted at room temperature for 2 hours. After the reaction is completed, the polystyrene ball is washed with 0.05M phosphate buffer containing 0.1M of NaCl and 1 mM of $MgCl_2$, the enzymatic reaction is then conducted and fluorescence intensity is measured. The standard curves are shown in FIG. 3. In FIG. 3,        denotes the standard curve of hCG, x the curve of hCG-β, □ the curve of hCG-α,        the curve of hLH, Δ the curve of hFSH, and        the curve of hTSH.

Thus, the assay method of this invention is specific to hCG only and does not show cross-reactivity with any of hCG-α, hCG-β, hLH, hFSH and hTSH.

EXAMPLE 5

(1) Production of a horseradish peroxidase-labeled anti-hCG antibody conjugate:

The method of Nakane et al. [Journal of Histochemistry and Cytochemistry, 22 (1974), P. 1084] is followed. In 1 ml of 0.3M sodium bicarbonate (pH 8.1) is dissolved 7 mg of horseradish peroxidase, followed by addition of 0.1 ml of 1% 1-fluoro-2,4-dinitrobenzene. The mixture is reacted at room temperature for an hour. Then, 1 ml of 0.06M $NaIO_4$ is added and the mixture is stirred at room temperature for 30 minutes. After addition of 1 ml of 0.16M aqueous ethylene glycol solution, the mixture is allowed to stand at room temperature for an hour. It is then dialyzed against 0.01M sodium carbonate buffer (pH 9.5) overnight and 1 ml of a solution of 1.8 mg of the specific hCG antibody prepared in Reference Example 5 in 0.01M carbonate buffer (pH 9.5) is added. The mixture is reacted at room temperature for 3 hours, after which 5 mg of $NaHB_4$ is added. The mixture is reacted at 4° C. overnight. The reaction mixture is dialyzed against 0.01M phosphate buffer (pH 7.1) containing 0.15M of NaCl at 4° C. overnight and the dialyzate is fractionated on a Sephadex G-200 column. By the above procedure is obtained a horseradish peroxidase-labeled anti-hCG conjugate.

(2) Production of an antibody-carrying solid phase:

To 300 polystyrene balls (6.4 mm dia., Precision Plastics Ball Co., Chicago, U.S.A.) is added 50 ml of 0.01M phosphate buffer (pH 7.7) and the system is warmed to 56° C. Then, 2.5 mg of the T7CS prepared in Example 1 (3) is added and the mixture is incubated at 56° C. for 2 hours. The balls are washed with 0.05M phosphate buffer (pH 7.0) containing 0.1% of BSA and stored in a refrigerator.

(3) Assay:

To 400 μl of 0.1M phosphate buffer containing 3% of normal rabbit serum is added 100 μl of the standard solution of hCG, hCG-α, hCG-β, hLH, hFSH or hTSH, and one of the anti-hCG antibody-polystyrene conjugate ball produced in Example 5 (2) is added. The reaction is conducted at room temperature for an hour. The polystyrene ball is then washed with 0.1M phosphate buffer, and 100 μl of the horseradish peroxidase-labeled specific anti-hCG antibody solution prepared in Example 5 (1) is added. The reaction is carried out at room temperature for 2 hours. After the reaction is completed, the polystyrene ball is washed with phosphate buffer, followed by addition of 2 ml of a substrate solution (in phosphate buffer, pH 7.0) containing 244 mg/dl of 4-aminoantipyrine, 800 mg/dl of phenol and 30 μl/dl of 30% aqueous hydrogen peroxide. The mixture is reacted at room temperature for 1.5 hours. The reaction is terminated with 25 μl of 20% $NaN_3$ and the absorption intensity at 507 nm is measured to construct the standard curve. The same relation as FIG. 2 is obtained. Thus, this assay is specific to hCG and hCG-β only and does not show cross-reactivity with hCG-α, hLH, hFSH, and hTSH.

EXAMPLE 6

The anti-hCG antibody-β-Gal conjugate according to Example 1 (3) is dissolved in the following buffers (aqueous solutions) (a) and (b). The concentration of β-Gal in each solution is 100 ng/ml.

(a) 0.05M Phosphate buffer (pH 7.0) containing 5 w/v % of sucrose, 0.2% of bovine serum albumin and 0.001M of $MgCl_2$.

(b) The same buffer as above except that sucrose is not contained.

Each of the above aqueous composition containing β-Gal is frozen at −40° C. and then lyophilized at 10° C. and ≦10 mmHg. The freeze-dried composition is purged well with nitrogen gas and sealed in a nitrogen atmosphere. This lyophilizate is stored at 10° C.

After 23 weeks, these lyophilizates are reconstituted. The enzymatic activity of the composition from lyophilizate (a) is substantially not different from initial value. A predetermined dilution (100 μl) of this liquid (which has a predetermined suitable enzymatic activity (ca. 1 mU/ml)] is admixed with 400 μl of 0.1M phosphate buffer containing 5% normal rabbit serum, 0.1% $NaN_3$ and 1 mM $MgCl_2$, 100 μl of a hCG-containing test fluid and a polystyrene ball to which anti-hCG-β C-terminal fragments peptide (123–145)-antibody has been supported [Example 1 (4)] and the reaction is carried out at room temperature for 2 hours. On completion of the reaction, the polystyrene ball is washed 3 times with 0.05M phosphate buffer containing 0.1M NaCl and 1 mM $MgCl_2$ and, then, 400 μl of a substrate solution (20 μg/ml of 4-methylumbelliferyl-β-D-galactopyranoside dissolved in 0.02M phosphate buffer containing 0.1% bovine serum albumin, 0.1% $NaN_3$, 0.1M NaCl and 1 mM $MgCl_2$) is added. The reaction is conducted at 37° C. for 2 hours and the fluorescence intensity of the reaction mixture is measured at the excitation wavelength of 365 nm and the fluorescent wavelength of 450 nm. The results of EIA runs by the sandwich method described hereinbefore are shown in FIG. 4 (In FIG. 4, -o- represents the values obtained with the composition from lyophilizate (a) and ─ represents the results with the unlyophilized β-Gal-containing aqueous composition.). It will be apparent from FIG. 4 that the composition reconstituted from lyophilizate (a) yields the same assay results as the unlyophilized β-Gal-containing composition. The composition reconstituted from lyophilizate (b) has an enzymatic activity as low as ≦10% of initial activity and cannot be utilized for EIA.

EXAMPLE 7

A conjugate of anti-human IgG antibody [Miles Laboratories, U.S.A.] and β-Gal (Journal of Immunology 116, 1554 (1976)] is treated in the manner as Example 6 to give lyophilizates (a) and (b).

After 12 weeks, the above lyophilizates are reconstituted. The enzymatic activity of the composition from lyophilizate (a) is substantially unchanged from the initial value. The results of EIA of human IgG by the sandwich method of Example 6 are shown in FIG. 5 (In FIG. 5, -o- represents the results obtained with the composition from lyophilizate (a) and ─ represents those obtained with the unlyophilized β-Gal-containing aqueous composition.) It will be apparent from FIG. 5 that the composition from lyophilizate (a) yields the same assay results as the unlyophilized β-Gal-containing aqueous composition. The composition from lyophilizate (b) has an enzymatic activity as low as ≦10% of initial activity and cannot be utilized for EIA.

EXAMPLE 8

The conjugate of anti-hCG antibody and β-Gal according to Example 1 (4) is treated in the manner as Example 6 except that 5% (w/v) sucrose in buffer (a) is replaced with 3% (w/v) lactose or galactose to give lyophilizates (a) and (b).

After 23 weeks, the lyophilizates are reconstituted. The enzymatic activity of the composition from the lactose- or galactose-containing lyophilizate (a) shows no change at all. Using this composition, an EIA of hCG is performed by the sandwich method described in Example 6. The results are shown in FIG. 6 [In FIG. 6, -Δ- represents the results obtained with the composition from the lactose-containing lyophilizate (a) and -□- represents the results obtained with the galactose-containing composition (a), ─ represents the results with the unlyophilized β-Gal-containing aqueous composition, and -x- represents the results with lyophilizate (b).]. It will be apparent from FIG. 6 that the composition from lyophilizate (a) yields the same assay results as the unlyophilized β-Gal-containing composition, and that the composition from the lyophilizate (b) obtained with the sugar-free buffer shows an enzymatic activity as low as ≦10% of initial activity and, therefore, cannot provide a calibration curve in EIA.

EXAMPLE 9

The immunochemical assay kit for hCG and the assay of hCG

Using the following immunochemical assay kit for hCG, the concentrations of hCG in urine and serum samples from normal humans, pregnant women are measured. The results are shown in Table 2.

(a) The immunochemical assay kit for hCG:

(1) Polystyrene balls, 6.4 mm in dia. sensitized with 6.7 μg/ball of anti-hCG-β C-terminal fragment peptide antibody which is obtained according to Example 1

(2) The portion having about 400 μU of the β-D-galactosidase-labeled anti-hCG antibody conjugate (3) 0 to 100 IU of standard hCG (4) 0.1M Phosphate buffer (pH 7.4) containing 5% of normal rabbit serum, 0.1% of $NaN_3$ and 1 mM of $MgCl_2$, which is used for diluting the reagents (2) and (3)

(5) 20 μg of 4-methylumbellipheryl-β-D-galactoside (6) 0.02M Phosphate buffer (pH 7.0) containing 0.1% of bovine serum albumin, 0.1% of $NaN_3$ and 1 mM of $MgCl_2$, which is used for dissolving the substrate (5)

(7) 0.05M Phosphate buffer (pH 7.0) containing 0.1M of NaCl and 1 mM of $MgCl_2$, which is used for washing the polystyrene ball (1)

(8) 0.1M Carbonate buffer (pH 10.5) (b) Assay: To 100 μl of standard hCG or test sample are added 400 μl of reagent (4), one ball of reagent (1) and 100 μl of reagent (2), and the mixture is reacted at room temperature for 2 hours. The polystyrene ball is then washed with reagent (7), followed by addition of 400 μl of reagent (5) so as to initiate the enzymatic reaction. This reaction is conducted at 37° C. for 2 hours, at the end of which time the reaction is terminated by addition of 2.5 ml of reagent (8). The intensity of fluorescence of the reaction mixture is measured to estimate the concentration of hCG in the test fluid.

The urinary and blood levels of hCG in normal subjects and pregnant women are determined by the above assay method. The results are set forth in Table 2.

TABLE 2

| Test Fluid | | Concentration of hCG (mIU/ml) |
|---|---|---|
| Normal human urine | 1 | <10 |
| | 2 | <10 |
| | 3 | <10 |
| | 4 | <10 |
| Pregnant human urine | 1 | 85000 |
| | 2 | 3400 |
| | 3 | 2000 |
| | 4 | 15500 |
| Normal human serum | 1 | <10 |
| | 2 | <10 |
| | 3 | <10 |
| | 4 | <10 |
| Pregnant human serum | 1 | 56000 |
| | 2 | 34000 |
| | 3 | 95000 |

EXAMPLE 10

Immunochemical hCG assay kit, and assay of hCG:

Using the following kit for immunochemical assays of hCG, the concentration of hCG in the urine or serum samples from normal humans, pregnant women and patient are measured in the following manner. The results are set forth in Table 3.

(a) Kit for Immunochemical Assay of hCG:

(1) Polystyrene balls, 6.4 mm in diameter, sensitized with 6.7 μg of anti-hCG-β C-terminal fragment peptide (123–145) per ball as prepared in accordance with Example 1:

(2) A portion equivalent to an enzymatic activity of about 400 μU of a lyophilizate of β-D-galactosidase-labeled anti-hCG antibody conjugate as prepared in accordance with Example 6;

(3) From 0 to 100 IU of standard hCG;

(4) 0.1M Phosphate buffer (pH 7.4) containing 5% of normal rabbit serum and 1 mM of $MgCl_2$ for the dilution of the above reagents (1) through (3) and the test fluid;

(5) 20 μg of 4-Methylumbelliferyl-β-D-galactoside;

(6) 0.02M Phosphate buffer (pH 7.0) containing 0.1% of bovine serum albumin, 0.1% of $NaN_3$ and 1 mM of $MgCl_2$ for dissolving the substrate (5);

(7) 0.05M Phosphate buffer (pH 7.0) containing 0.1M of NaCl and 1 mM of $MgCl_2$ for washing polystyrene balls (1);

(8) 0.1M Carbonate buffer, pH 10.5. (b) Procedure:

To 100 μl of standard hCG or test fluid are added one ball of reagent (1) and 100 μl of reagent (2), and the reaction is conducted at room temperature for 2 hours. The polystyrene ball is washed with reagent (7) and, then, 400 μl of reagent (5) is added to initiate the enzymatic reaction. This reaction is conducted at 37° C. for 2 hours, at the end of which time 2.5 ml of reagent (8) is added so as to terminate the reaction. The fluorescence intensity of the reaction system is measured to estimate the titer of hCG in the test fluid. The results are set forth in Table 3.

TABLE 3

| Test Sample | | Titer of hCG (mIU/ml) |
|---|---|---|
| Normal human urine | 1 | <5 |
| | 2 | <5 |
| | 3 | <5 |
| | 4 | <5 |
| Urine of pregnant woman | 1 | 80000 |
| | 2 | 3400 |
| | 3 | 2000 |
| | 4 | 15000 |
| Normal human serum | 1 | <5 |
| | 2 | <5 |
| | 3 | <5 |
| | 4 | <5 |
| Serum of pregnant woman | 1 | 56000 |
| | 2 | 34000 |
| | 3 | 91000 |
| Serum of pregnant woman in early pregnancy | 1 | 48 |
| | 2 | 52 |
| | 3 | 252 |
| | 4 | 170 |
| | 5 | 74 |
| Serum of woman with mola delivery | 1 | 62 |
| | 2 | 84 |
| | 3 | 38 |
| | 4 | 71 |
| | 5 | 325 |

Further, pre- and postoperative serum hCG levels in a patient with hydatidiform mole are measured by using the assay kit for hCG. Postoperative hCG levels are lower gradually and less than 5 mIU/ml at five weeks. The results are shown in FIG. 7.

What we claim is:

1. In a method for immunochemical assay of human chorionic gonadotropin using an antibody immobilized on a carrier, an antigen and an antibody coupled with a labeling agent, the improvement which comprises using as the antibody to be immobilized on the carrier and the antibody to be coupled with the labeling agent different antibodies which are not overlapping in antigen-determining site, and wherein one of said different antibodies is specifically reactive to human chorionic gonadotropin, said specifically reactive antibody being obtained by contacting a peptide of the formula:

H-R-Pro-Ser-Asp-Thr-Pro-Ile-Leu-Pro-Gln-OH wherein R is a partial peptide of 1 to 14 amino acid residues including 14-Gly of the peptide $Ala^1$-$Pro^2$-$Pro^3$-$Pro^4$-$Ser^5$-$Leu^6$-$Pro^7$-$Ser^8$-$Pro^9$-$Ser^{10}$-$Arg^{11}$-$Leu^{12}$-$Pro^{13}$-$Gly^{14}$, as immobilized on a carrier, with a body fluid containing an anti-human chorionic gonadotropin antibody, and eluting the anti-human chorionic gonadotropin antibody thus specifically absorbed.

2. The improvement as claimed in claim 1, wherein the antibody immobilized on the carrier and the antibody coupled with the labeling agent are simultaneously reacted with the antigen.

3. The improvement as claimed in claim 1, wherein the labeling agent is a radioisotope, enzyme, fluorescent substance, or luminous substance.

4. The improvement as claimed in claim 3, wherein the radioisotope is $^{125}I$, $^{131}I$, $^3H$ or $^{14}C$.

5. The improvement as claimed in claim 3, wherein the labeling agent is β-galactosidase, alkaline phosphatase or, horseradish peroxidase.

6. The improvement as claimed in claim 1, wherein the peptide is H-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln-OH.

7. An assay kit for immunochemical assay of hCG by the sandwich method, which comprises, in containers (1) An antibody immobilized on a carrier, (2) An antibody labeled with a labeling agent, wherein the antibody used in reagent (1) and the antibody used in reagent (2) are different antibodies which are not overlapping in antigen-determining site, and one of said different antibodies is specifically reactive to human chorionic gonadotropin; said specifically reactive antibody being obtained by contacting a peptide of the formula:

H-R-Pro-Ser-Asp-Thr-Pro-Ile-Leu-Pro-Gln-OH wherein R is a partial peptide of 1 to 14 amino acid residues including 14-Gly of the peptide $Ala^1$-$Pro^2$-$Pro^3$-$Pro^4$-$Ser^5$-$Leu^6$-$Pro^7$-$Ser^8$-$Pro^9$-$Ser^{10}$-$Arg^{11}$-$Leu^{12}$-$Pro^{13}$-$Gly^{14}$, as immobilized on a carrier, with a body fluid containing an anti-human chorionic gonadotropin antibody, and eluting the anti-human chorionic gonadotropin antibody thus specifically absorbed, (3) A standard hCG of 0 to 100 IU, (4) A buffer for dilution of reagents (1) to (3) and a test fluid, (5) A buffer for use in washing the carrier after incubation, and (6) When the labeling agent is an enzyme, reagents used in measuring the activity of the enzyme; When a fluorescent substance is used as the labeling agent, materials for measuring the intensity of fluorescence; When a luminous substance is used as the labeling agent, an oxidizing agent, catalyst and buffer for dissolving the oxidizing agent and catalyst.

8. The assay kit as claimed in claim 4, wherein the antibody labeled with the labeling agent is a lyophilizate of an anti-hCG antibody-β-galactosidase conjugate.

* * * * *